(12) United States Patent
Takahashi et al.

(10) Patent No.: US 10,542,870 B2
(45) Date of Patent: Jan. 28, 2020

(54) MANIPULATOR

(71) Applicant: OLYMPUS CORPORATION, Tokyo (JP)

(72) Inventors: Keigo Takahashi, Tokyo (JP); Kosuke Kishi, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 185 days.

(21) Appl. No.: 15/682,627

(22) Filed: Aug. 22, 2017

(65) Prior Publication Data

US 2017/0347863 A1 Dec. 7, 2017

Related U.S. Application Data

(63) Continuation of application No. PCT/JP2016/051036, filed on Jan. 14, 2016.

(30) Foreign Application Priority Data

Feb. 25, 2015 (JP) .................................. 2015-035322

(51) Int. Cl.
*A61B 17/28* (2006.01)
*A61B 1/00* (2006.01)
(Continued)

(52) U.S. Cl.
CPC ...... *A61B 1/00133* (2013.01); *A61B 1/00087* (2013.01); *A61B 1/00149* (2013.01);
(Continued)

(58) Field of Classification Search
CPC ............ A61B 1/00066; A61B 1/00087; A61B 1/00105; A61B 1/00133; A61B 1/00149;
(Continued)

(56) References Cited

U.S. PATENT DOCUMENTS 5,876,325 A 3/1999 Mizuno et al.
8,157,793 B2 * 4/2012 Omori .................... A61B 17/29
606/1

(Continued)

FOREIGN PATENT DOCUMENTS

EP 2 324 789 A1 5/2011
JP H07-328024 A 12/1995
(Continued)

OTHER PUBLICATIONS

Extended Supplementary European Search Report dated Jan. 3, 2019 in European Patent Application No. 16 75 5068.0.
(Continued)

*Primary Examiner* — Ryan J. Severson
(74) *Attorney, Agent, or Firm* — Scully, Scott, Murphy & Presser, P.C.

(57) ABSTRACT

A manipulator, including:
 a drive unit for generating a driving force, and
 a treatment tool that is driven by the drive unit and attachable to and detachable from the drive unit, wherein the treatment tool includes:
 a distal end having at least one joint driven by the drive unit,
 a lock unit that is actuated to lock at least one of joints at the distal end,
 a lock-operating unit for operating the lock unit, and
 a control unit that is operated such that the lock unit is operated by the lock-operating unit and such that when the drive unit is driven, the drive unit is deactivated, and even with the treatment tool detached from the drive unit, the lock unit keeps on with locking.

7 Claims, 27 Drawing Sheets

(51) Int. Cl.
*B25J 1/02* (2006.01)
*A61B 90/00* (2016.01)
*A61B 34/00* (2016.01)
*A61B 17/00* (2006.01)
*B25J 3/04* (2006.01)
*B25J 13/02* (2006.01)
*B25J 18/00* (2006.01)
*B25J 18/06* (2006.01)

(52) U.S. Cl.
CPC ........ *A61B 17/00234* (2013.01); *A61B 17/28* (2013.01); *A61B 34/70* (2016.02); *A61B 90/00* (2016.02); *B25J 1/02* (2013.01); *B25J 3/04* (2013.01); *B25J 13/02* (2013.01); *B25J 18/007* (2013.01); *B25J 18/06* (2013.01)

(58) Field of Classification Search
CPC ................ A61B 1/0016; A61B 1/0052; A61B 17/00234; A61B 17/28; A61B 17/2833; A61B 17/29; A61B 17/2909; A61B 2017/00296; A61B 2017/0034; A61B 2017/00367; A61B 2017/00398; A61B 2017/0046; A61B 2017/00477; A61B 2017/00818; A61B 2017/2946; A61B 2034/301; A61B 2034/303; A61B 34/35; A61B 34/37; A61B 34/70; A61B 34/72; A61B 34/74; A61B 34/75
See application file for complete search history.

(56) References Cited

U.S. PATENT DOCUMENTS

| | | | | |
|---|---|---|---|---|
| 8,246,608 B2* | 8/2012 | Omori | ................... | A61B 34/71 606/1 |
| 8,409,175 B2* | 4/2013 | Lee | ..................... | A61B 17/062 600/114 |
| 8,500,721 B2* | 8/2013 | Jinno | .................... | A61B 34/70 606/1 |
| 9,408,606 B2* | 8/2016 | Shelton, IV | ..... | A61B 17/07207 |
| 9,532,794 B2* | 1/2017 | Jinno | ................. | A61B 17/2909 |
| 9,730,717 B2* | 8/2017 | Katsuki | .................. | A61B 17/29 |
| 9,802,324 B2* | 10/2017 | Iida | ........................ | A61B 34/37 |
| 10,005,181 B2* | 6/2018 | Hasegawa | .............. | B25J 9/1612 |
| 10,045,791 B2* | 8/2018 | Sakaguchi | ......... | A61B 18/1445 |
| 10,149,726 B2* | 12/2018 | Hibner | .................. | A61B 34/20 |
| 10,155,316 B2* | 12/2018 | Wakai | .................... | B25J 9/1692 |
| 10,182,874 B2* | 1/2019 | Hasegawa | ................ | A61B 1/00 |
| 10,194,999 B2* | 2/2019 | Bacher | ...................... | A61N 5/00 |
| 2008/0103491 A1 | 5/2008 | Omori et al. | | |
| 2009/0062814 A1* | 3/2009 | Omori | .................... | A61B 34/70 606/130 |
| 2009/0299344 A1 | 12/2009 | Lee et al. | | |
| 2011/0015650 A1 | 1/2011 | Choi et al. | | |
| 2012/0203269 A1* | 8/2012 | Katsuki | .................. | A61B 17/29 606/205 |
| 2013/0338647 A1* | 12/2013 | Bacher | ..................... | A61N 5/00 606/1 |
| 2014/0001235 A1 | 1/2014 | Shelton, IV | | |
| 2015/0127019 A1* | 5/2015 | Komuro | .................. | A61B 34/30 606/130 |
| 2016/0374772 A1* | 12/2016 | Hasegawa | ................ | A61B 1/00 606/130 |
| 2017/0347863 A1* | 12/2017 | Takahashi | .............. | A61B 17/28 |

FOREIGN PATENT DOCUMENTS

| | | |
|---|---|---|
| JP | 2009-213653 A | 9/2009 |
| JP | 2010-012087 A | 1/2010 |
| JP | 2010-022415 A | 2/2010 |
| JP | 2010-220955 A | 10/2010 |
| JP | 2013-215507 A | 10/2013 |
| WO | WO 2014/021222 A1 | 2/2014 |

OTHER PUBLICATIONS

International Search Report dated Apr. 5, 2016 issued in PCT/JP2016/051036.

* cited by examiner

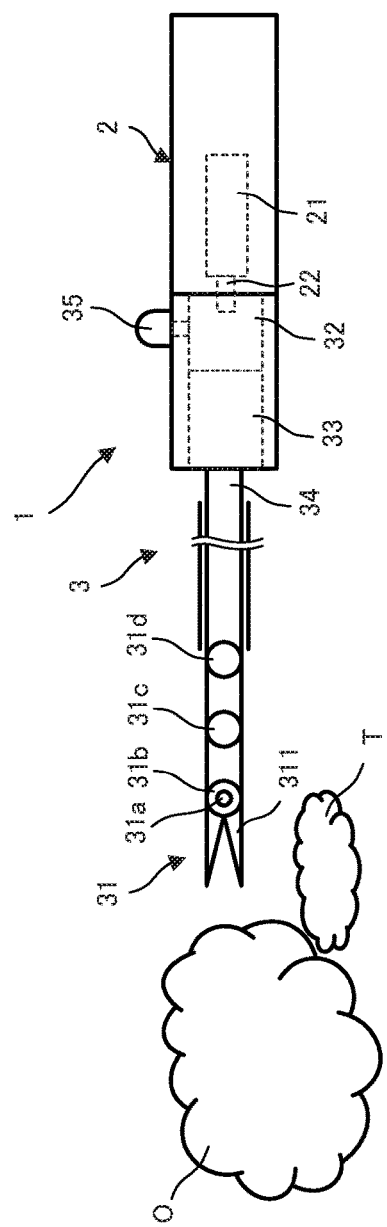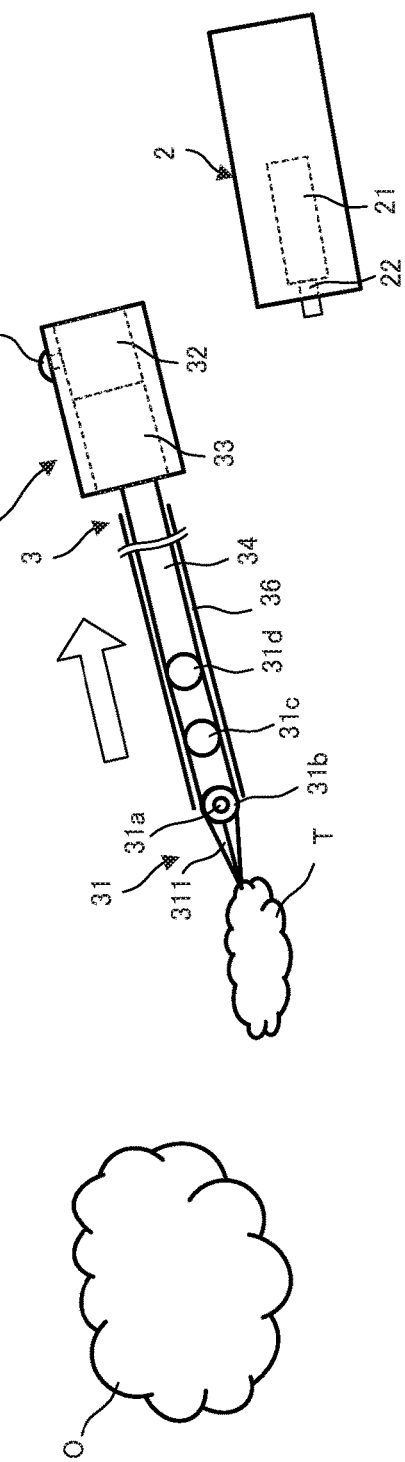

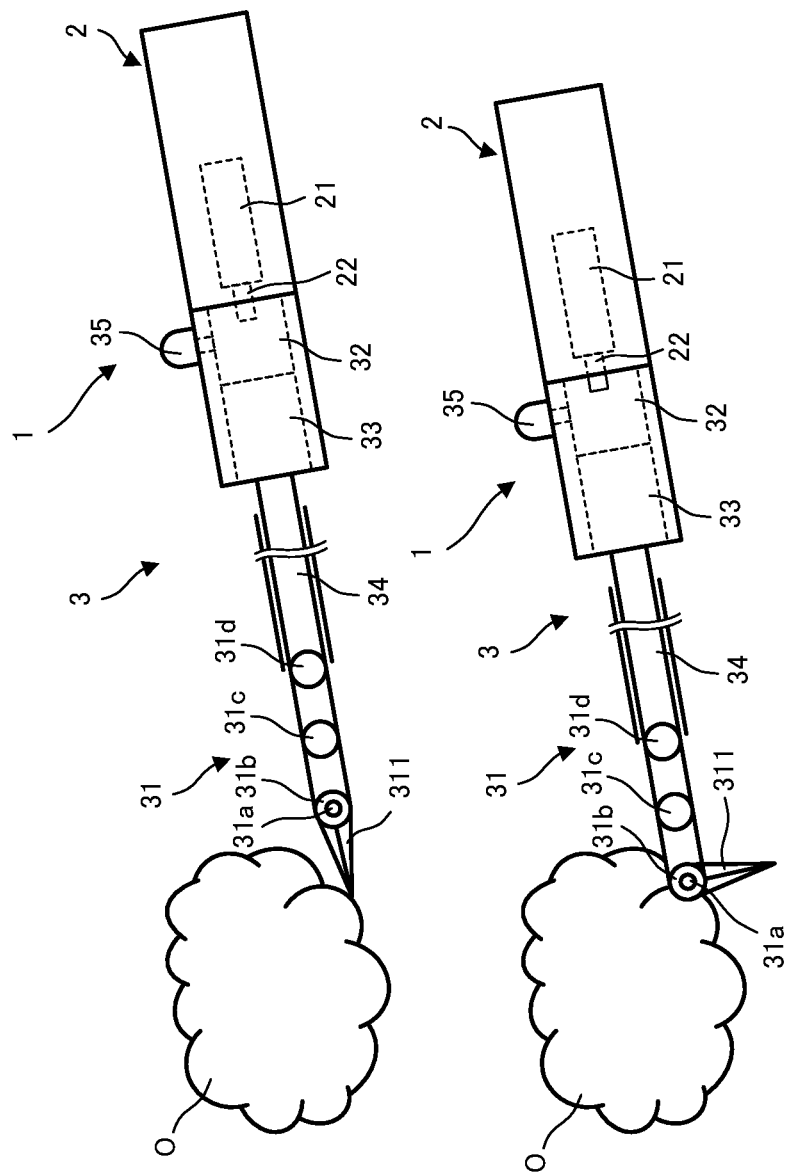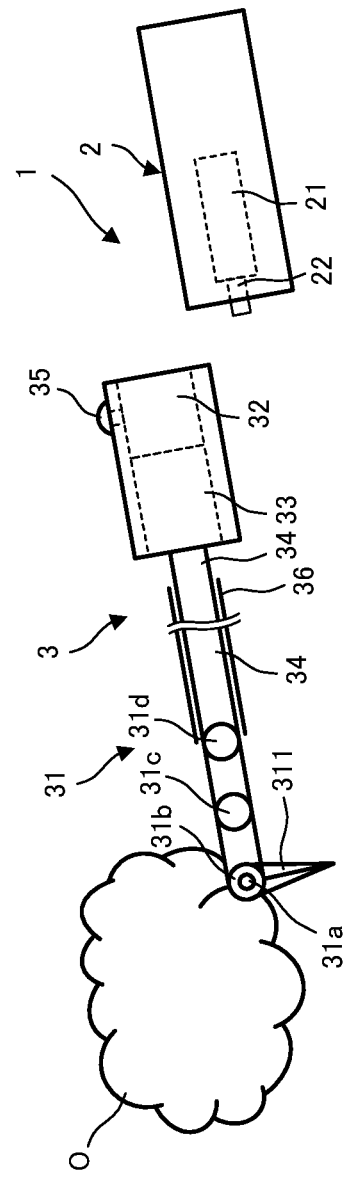
FIG.12A
FIG.12B
FIG.12C

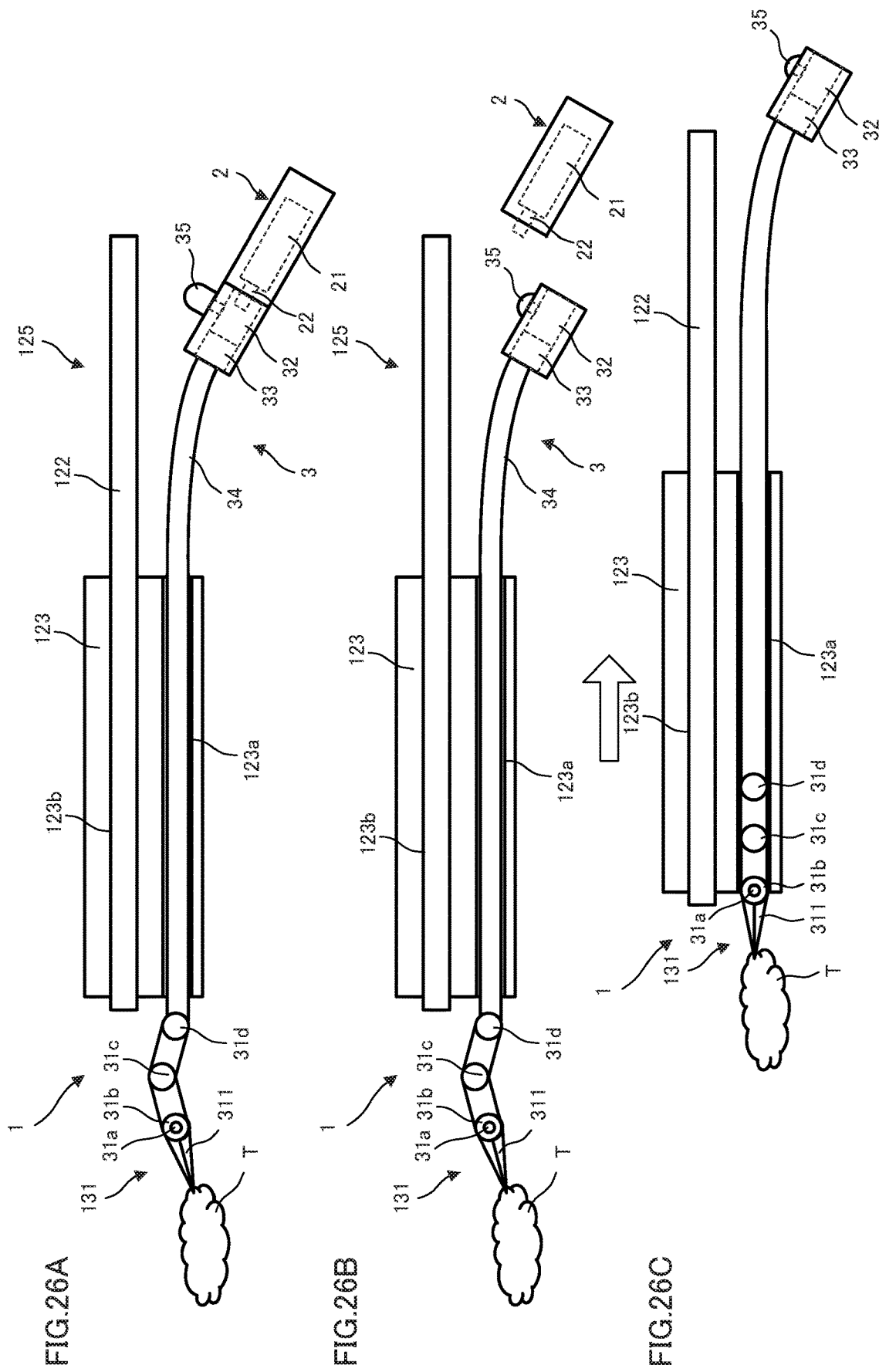

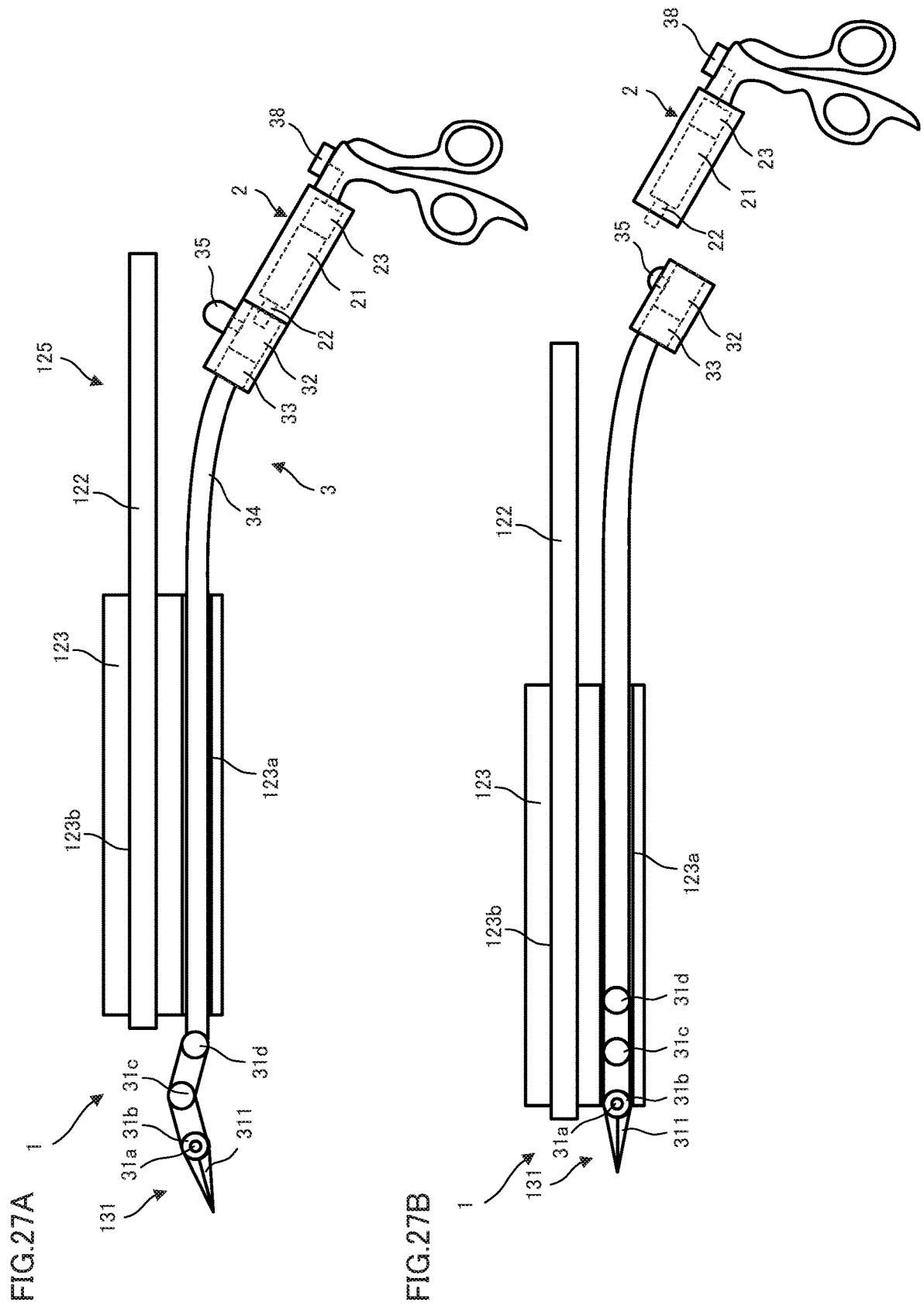

MANIPULATOR

CROSS-REFERENCE TO RELATED APPLICATIONS

This application is a continuation claiming priority on the basis of Japan Patent Application No. 2015-035322 applied in Japan on Feb. 25, 2015 and based on PCT/JP2016/051036 filed on Jan. 14, 2016. The contents of both the PCT application and the Japan Application are incorporated herein by reference.

BACKGROUND OF THE INVENTION AND RELATED ART STATEMENT

The present invention relates to a treatment tool and a manipulator that is inserted through a patient for surgical operations or the like to apply treatments or the like thereto.

There have widely been medical equipments used that include a treatment tool inserted through the body cavity of a patient to pull its distal end as by a wire for viewing, and applying treatments to, internal organs in the body cavity. Such a treatment tool has a structure having a sufficient force albeit being of small diameter and size enough to gain access to the interior of the body cavity.

JP(A) 2010-12087 discloses a manipulator that may be used in the medical field to prevent force from decreasing and reduce force consumptions.

SUMMARY OF INVENTION

A manipulator according to one embodiment includes:
a drive unit for generating a driving force, and a treatment tool that is driven by the drive unit and attachable to and detachable from the drive unit, wherein the treatment tool includes:
a distal end having at least one joint driven by the drive unit, and
a lock unit that is actuated to lock at least one of joints at the distal end,
a lock-operating unit for operating the lock unit, and
a control unit that is operated such that the lock unit is operated by the lock-operating unit and such that when the drive unit is driven, the drive unit is deactivated, and even and even with the treatment tool detached from the drive unit, the lock unit keeps on with locking.

BRIEF DESCRIPTION OF DRAWINGS

FIGS. 7A, 7B and 7C show the first example of the manipulator according to the second embodiment.

FIGS. 12A, 12B and 12C show the fourth example of the manipulator according to the second embodiment.

FIGS. 26A, 26B and 26C show the actuation of the insert assembly according to a specific embodiment.

FIGS. 27A and 27B show the actuation of the insert assembly according to a specific embodiment.

DESCRIPTION OF EMBODIMENTS

Some embodiments will now be explained.

Figure 1A:
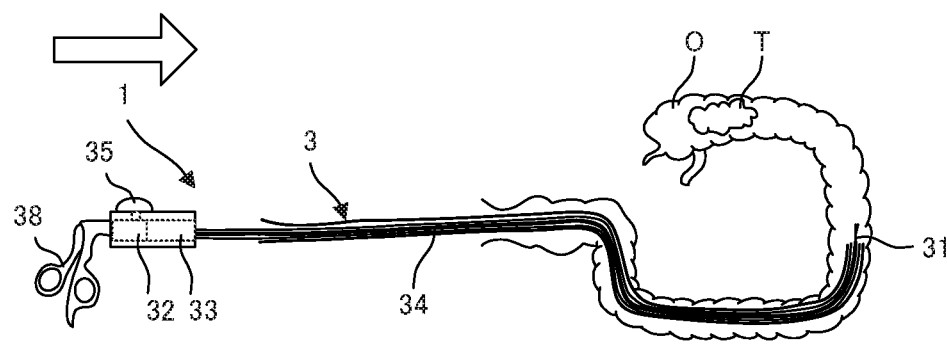
FIGS. 1A, 1B, 1C and 1D show an example of the manipulator in work according to the first embodiment.
Figure 1B:
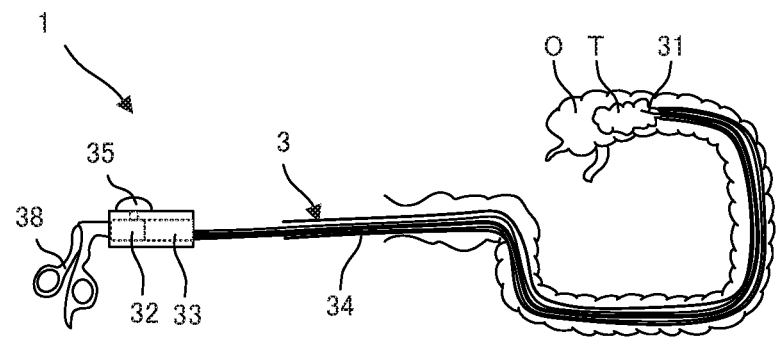
Figure 1C:
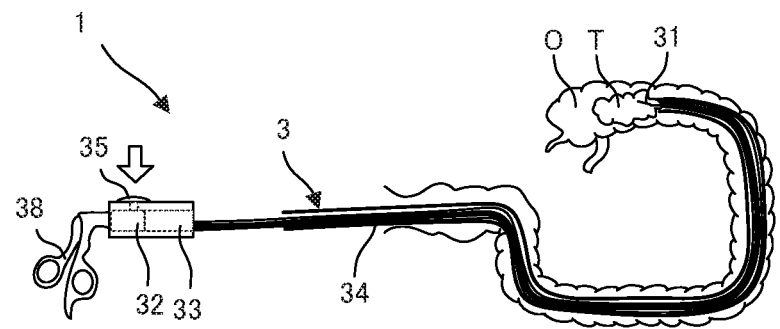
Figure 1D:
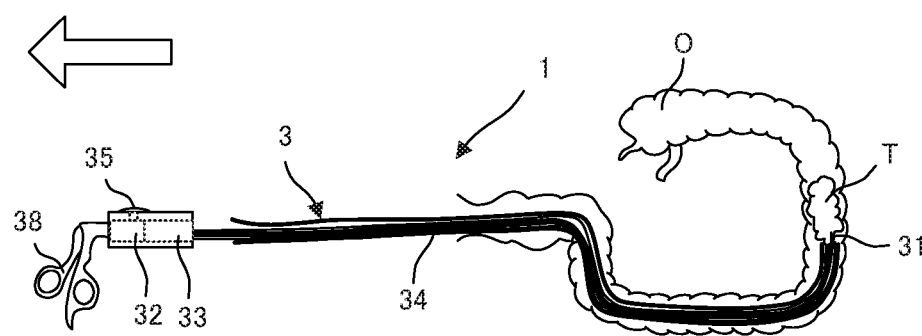

FIGS. 1A, 1B, 1C and 1D illustrate an example of the manipulator in work according to the first embodiment: FIG. 1A is illustrative of the manipulator being inserted in place, FIG. 1B is illustrative of the distal end reaching to a position of the end tissue piece T, FIG. 1C illustrates that the joints of the distal end 31 are deactivated, and FIG. 1D is illustrative of pulling a treatment tool 3.

The manipulator 1 according to the first embodiment includes a treatment tool 3. FIGS. 1A, 1B, 1C and 1D are illustrative of an exemplary basic working of the manipulator 1 here for excising a tissue piece T from an internal organ O and taking out it.

The treatment tool 3 includes a distal end 31 having at least one joint, a lock unit 32 that locks at least one of the joints at the distal end 31, a driving force transmission unit 33 for transmission of a driving force to the distal end 31, an elongated member 34 that couples the distal end 31 to the driving force transmission unit 33 and is bendable, a treatment tool-operating unit 38 for manual operations such as bending and grasping of the distal end 31, and a lock-operating unit 35 to use the locking unit 32 to lock the joints at the distal end 31. Note here that the wording "locking of the joints" means that the joints remain fixed in the current state. In other words, where the joints are locked in place, they remain fixed even when put into operation.

How to use the lock unit 32 of the manipulator 1 according to the first embodiment is now explained.

Figure 2:
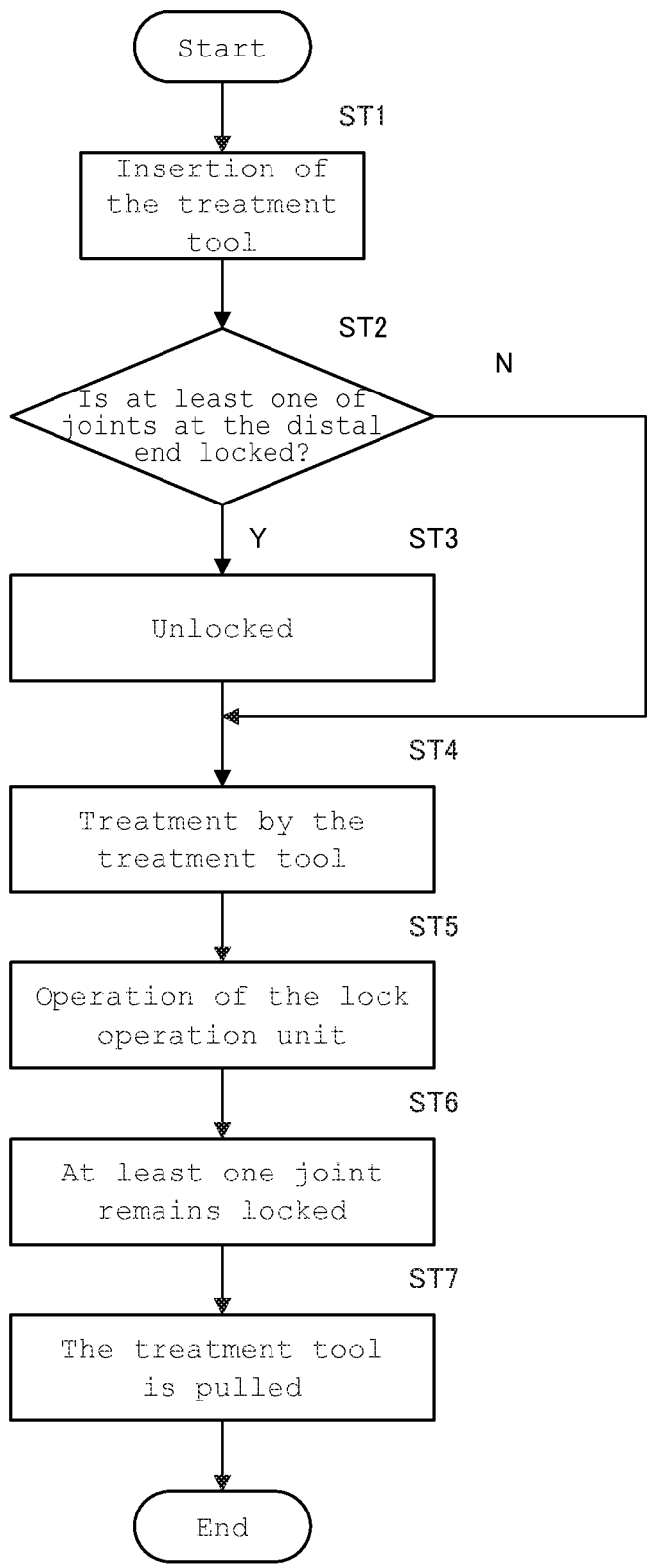
FIG. 2 is an actuation flowchart for how to lock the distal end of the manipulator according to the first embodiment.

FIG. 2 is an actuation flowchart illustrative of how to lock the distal end 31 of the manipulator 1 according to the first embodiment. The flowchart of FIG. 2 illustrates an example of the manipulator 1 in work wherein a tissue piece T excised out from an internal organ O and taken out, as shown in FIGS. 1A, 1B, 1C and 1D.

First of all, the treatment tool 3 is inserted through the body cavity in Step 1 as shown in FIG. 1A, and then advanced to a position of the end tissue piece T as shown in FIG. 1B (ST1).

In Step 2, an operator then identifies whether or not at least one of the joints at the distal end 31 is locked by the lock unit 32 of the treatment tool 3 (ST2). If the joint at the distal end 31 is identified to be not locked by the lock unit 32, the process goes to Step 4.

In Step 2, if at least one of the joints at the distal end 31 is identified to be locked by the lock unit 32, the process goes to Step 3 to unlock that joint (ST3).

Then, the process goes to Step 4 in which, in the state of FIG. 1B, the operator or an assistant puts the treatment tool-operating unit 38 into operation to apply various treatments via the treatment tool 3 (ST4). In this example, the tissue piece T is excised out from the internal organ O and grasped.

Then, the process goes to Step 5 in which the lock unit 32 is operated by the operator by way of the lock-operating unit 35 (ST5).

Thereupon, the process goes to Step 6, allowing the lock unit 32 to lock at least one of the joints at the distal end 31 (ST6). In this example, that joint is locked with the tissue piece T grasped at the distal end 31, while the joint configuration is fixed.

Then, the process goes to Step 7 in which, as shown in FIG. 1D, the treatment tool 3 is taken out while at least one of the joints at the distal end 31 remains locked (ST8). In this example, the treatment tool 3 is taken out while the tissue piece T is grasped and locked by the distal end 31 so that the tissue piece T can be taken out.

As mentioned above, the treatment tool 3 can be pulled while at least one of the joints at the distal end 31 remains locked. In this example, therefore, when the tissue piece T is taken out of the body after use of the treatment tool 3 in the body, the treatment tool 3 can be pulled while the tissue piece T is grasped and locked by the distal end 31 so that the tissue piece T can easily be taken out of the body.

A specific example of the manipulator 1 according to the first embodiment will now be explained.

Figure 3A:
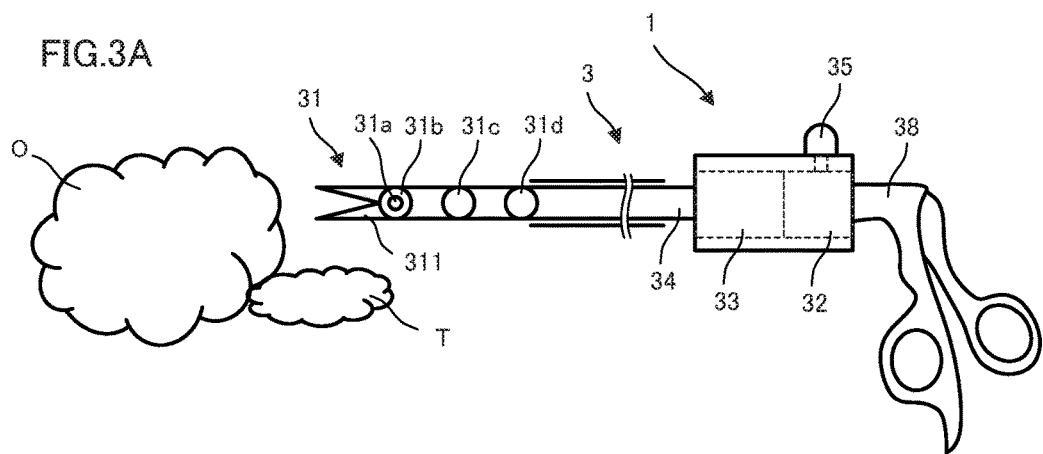
FIGS. 3A, 3B and 3C show the first example of the manipulator according to the first embodiment.
Figure 3B:
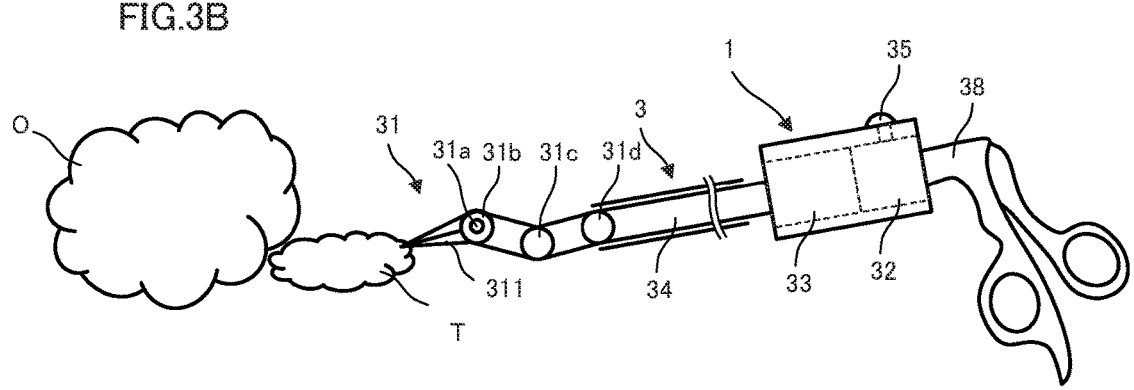
Figure 3C:
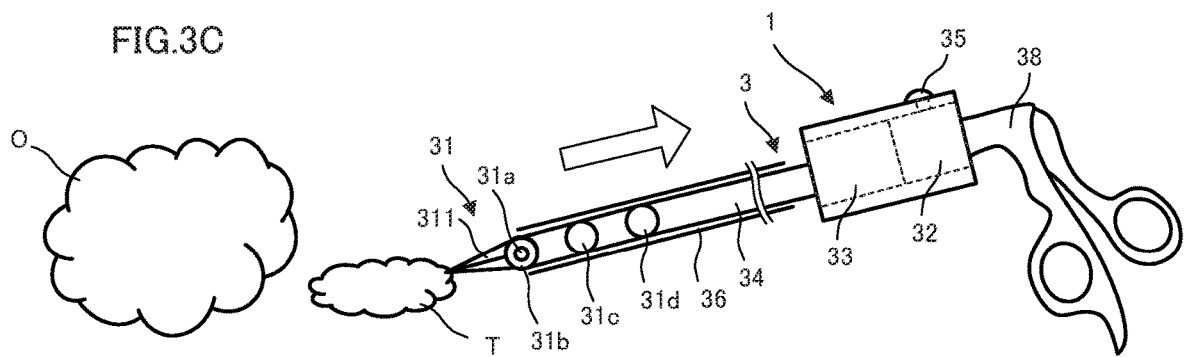

FIGS. 3A, 3B and 3C show a first example of the manipulator 1 according to the first embodiment. Note here that the manipulator 1 described just below has much the same arrangement as explained with reference to FIGS. 1A, 1B, 1C and 1D: that same arrangement will not be referred to anymore.

As shown in FIGS. 3A, 3B and 3C, the manipulator 1 according to the first example includes an open/close grasping part 311 at the distal end 31, and the distal end 31 includes a first joint 31a that is operated and rotated by an operator to open or close the grasping part 311 and a plurality of second to fourth joints 31b to 31d that are operated and rotated by the operator. The operator may operate and rotate the first joint 31a to open or close the grasping part 311 thereby grasping the tissue piece T or the like. As the second 31b, third 31c and fourth joint 31d rotate together, the distal end 31 changes in configuration. It is here to be noted that the end effector attached to the distal end 31 is not limited to the grasping part 311; it may be any desired treatment equipment such as an electric scalpel or an injector.

As also shown in FIGS. 3A, 3B and 3C, the manipulator 1 according to the first example is configured such that at least one of the joints at the distal end 31 can be locked. As the distal end 31 is locked, it enables the treatment tool 3 to be pulled out of the body while the tissue piece T remains grasped by the grasping part 311, making it easy to take the tissue piece T out of the body.

Figure 4:
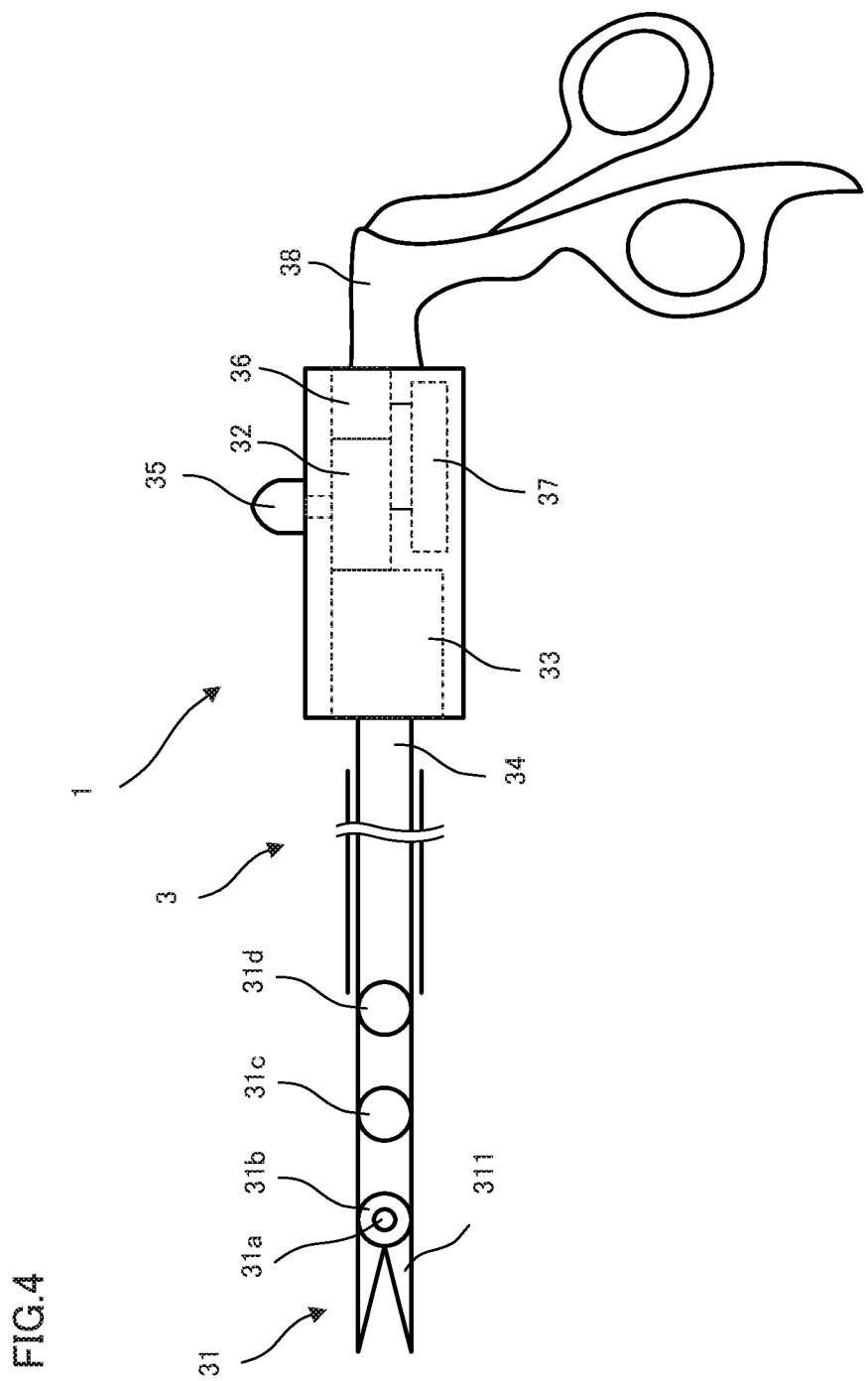
FIG. 4 shows the second example of the manipulator according to the first embodiment.

FIG. 4 shows the manipulator 1 of the second example according to the first embodiment.

The manipulator 1 of the second example according to the first embodiment includes an assist drive unit 36 adapted to assist the distal end 31 in adding a driving force to an operating force during manual operation, and an assist control unit 37 for controlling the assist drive unit 36.

When the operating force with which the operator operates the manipulator 1 exceeds a predetermined value, the assist drive unit 36 is driven by the assist control unit 37 to add the assist driving force to the operating force of the treatment tool-operating unit 38.

As is the case with the aforesaid example, the manipulator 1 here includes the lock unit 32 and lock-operating unit 35. In association with the operation of the lock-operating unit 35, the assist control unit 37 determines whether or not the driving force of the assist drive unit 36 is to be transmitted to the distal end. The lock unit 32 is designed to lock the distal end 31 so that even during operation of the manipulator 1 by the operator, the distal end 31 is prevented from inadvertent movement. Even with the manipulator 1 equipped with the assist drive unit 36, this makes the actuation state of the distal end 31 changeable so that it is easy to take the tissue piece T (not shown) out of the body.

The manipulator 1 here may also include an attachment/detachment portion detachable out of the assist drive unit 36. Further, the manipulator 1 may be replaced with a manually operating portion having a detachment portion similar to the assist drive unit 36 so that there can be a treatment tool desired for the operator provided while making a changeover between the relatively heavy drive unit 36 and the light manual drive unit.

FIGS. 5A, 5B, 5C and 5D are illustrative of an example of the manipulator in work according to the second embodiment.

The manipulator 1 according to the second embodiment includes a drive unit 2 for generating a driving force, and a treatment tool 3 that is driven by the drive unit 2 and attachable to or detachable from the drive unit 2. FIGS. 5A, 5B, 5C and 5D are illustrative of an exemplary basic working of the manipulator 1 here for resecting a tissue piece T out from an internal organ O and taking out it.

The drive unit 2 includes at least one drive member 21 and an output shaft 22 for producing out a driving force for each drive member 21.

The treatment tool 3 includes a distal end 31 having at least one joint driven by the drive unit 2, a lock unit 32 for blocking off transmission of a driving force to enable at least one of joints at the distal end 31 to be locked in place, a driving force transmission unit 33 for transmission of a driving force generated by the drive unit 2 to the distal end 31, an elongated member 34 that couples the distal end 31 to the driving force transmission unit 33 and is bendable, and a lock-operating unit 35 for blocking off transmission of a driving force by the lock unit 32.

Preferably, the manipulator 1 includes a control unit (not shown) to control the driving of the driving unit 2 in association with the operation of the lock-operating unit 35 thereby controlling the actuation state of the distal end 31.

How to use the lock unit 32 of the manipulator 1 according to the second embodiment will now be explained.

Figure 5A:
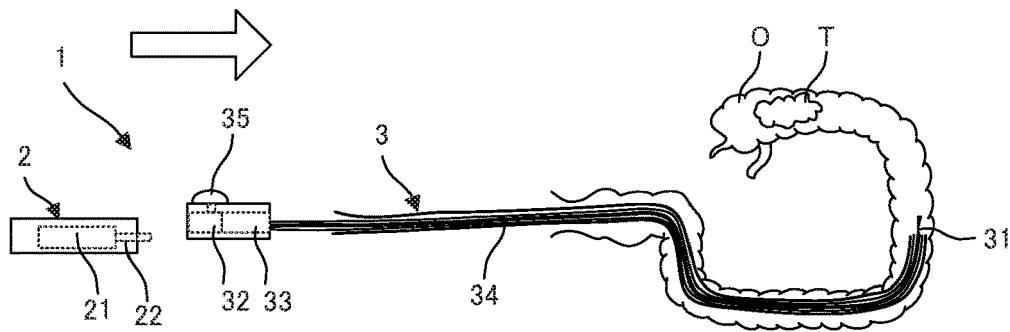
FIGS. 5A, 5B, 5C and 5D show an example of the manipulator in work according to the second embodiment.
Figure 5B:
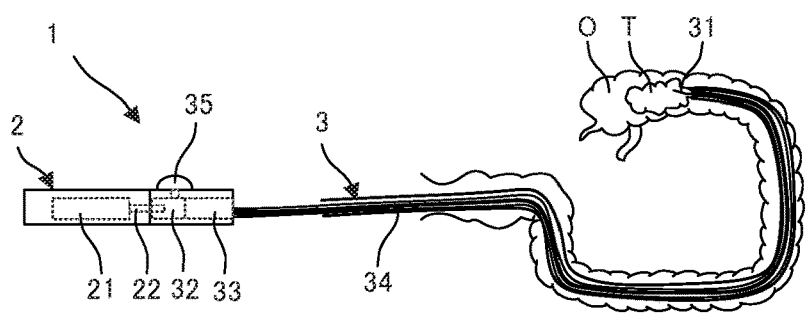
Figure 5C:
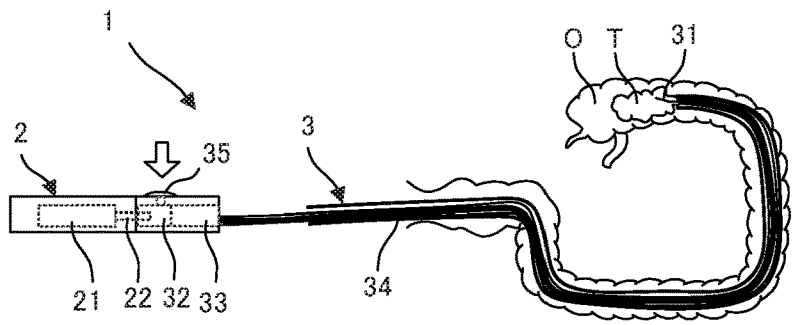
Figure 5D:
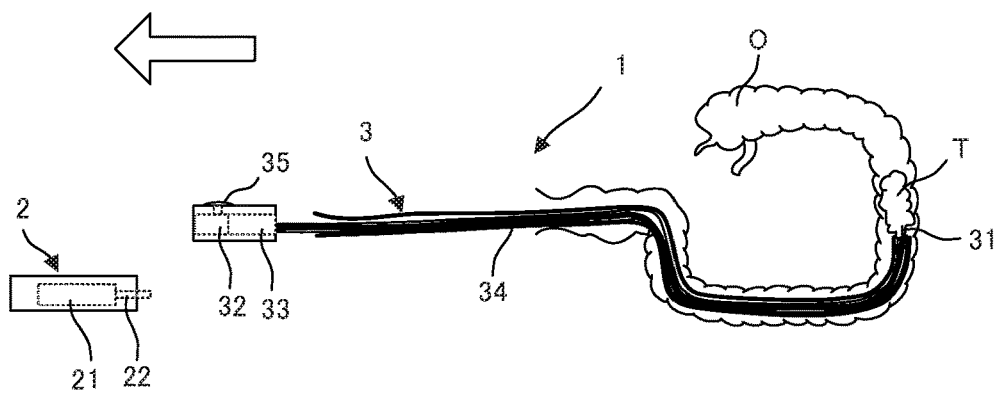
Figure 6:
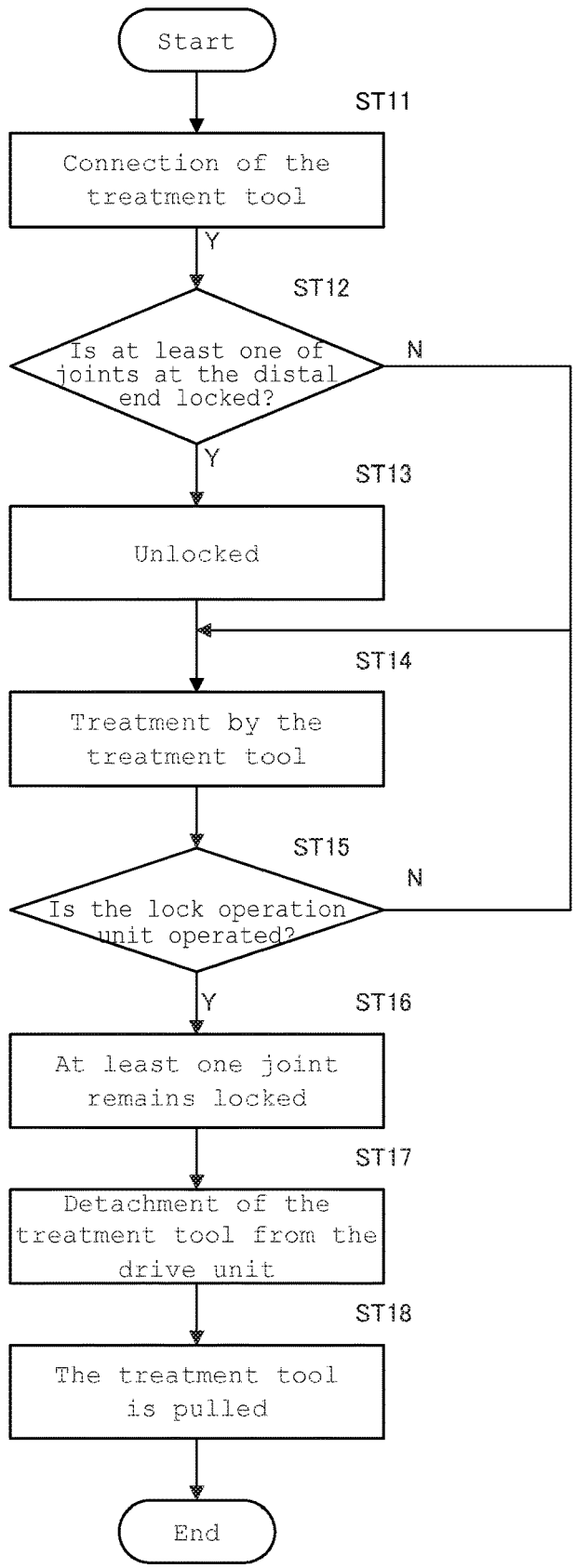
FIG. 6 is an actuation flowchart for how to lock the distal end of the manipulator according to the second embodiment.

FIG. 6 is an actuation flowchart of how to lock the distal end 31 of the manipulator 1 according to the second embodiment: the flowchart of FIG. 6 shows a working example of excising a tissue piece T out of an internal organ O and taking out it, as shown in FIGS. 5A, 5B, 5C and 5D.

In Step 11, the treatment tool 3 is first inserted through the body with no drive unit 2 attached to it, as shown in FIG. 5A, and then advanced to a position of the end tissue piece T as shown in FIG. 5B, after which the drive unit 2 is connected to the treatment tool 3 to place it in an enabled state (ST11).

In Step 12, whether or not at least one of the joints at the distal end 31 is locked by the lock unit 32 of the treatment tool 3 is then determined (ST12). In Step 2, if at least one of the joints at the distal end 31 is determined to be not locked by the lock unit 32, the process goes to Step 14.

In Step 12, if at least one of the joints at the distal end 31 is determined to be locked by the lock unit 32, the process goes to Step 13 in which the lock unit 32 is unlocked by operation of the lock-operating unit 35 (ST13).

In Step 14, the drive unit 2 is then driven in association with an operating input entered via the control unit (not shown) in a state of FIG. 5B, allowing an operator or assistant to use the treatment tool 3 for various treatments (ST14). In this example, the tissue piece T is excised out of the internal organ O and grasped.

Then, the process goes to Step 15 in which whether or not the lock-operating unit 35 is put into operation during the processing of Step 14 is monitored to determine whether or not the lock-operating unit 35 is in operation (ST15). In Step 15, if the lock-operating unit 35 is determined to be not in operation, the process goes back to Step 14, allowing the treatment tool 3 to keep on with treatment.

In Step 15, if the lock-operating unit 35 is determined to be in operation as shown in FIG. 5C, the process goes to Step 16 in which the transmission of driving force is blocked off to lock at least one of the joints at the distal end 31 (ST16). In this example, that joint is locked while the tissue piece T is grasped by the distal end 31, and the joint configuration remains fixed.

In Step 17, the treatment tool 3 is then detached from the drive unit 2 as shown in FIG. 5D (ST17). In this example, the treatment tool 3 is detached from the drive unit 2 so that after detachment from the drive unit 2, the joint at the distal end of the treatment tool 3 remains locked and the treatment tool 3 becomes light in weight for that and easy to operate alone.

In Step 18, the treatment tool 3 is pulled while at least one of the joints at the distal end 31 remains locked, as shown in FIG. 5D (ST18). In this example, the treatment tool 3 is pulled, together with the tissue piece T, while the distal end 31 remains locked with the tissue piece T grasped in place.

As described above, the treatment tool 3 may be pulled while at least one of the joints at the distal end 31 remains locked. It is thus possible to easily pull the treatment tool 3 out of the body after use of the treatment tool 3 in the body.

A specific example of the manipulator 1 according to the second embodiment will now be explained.

Figure 8:
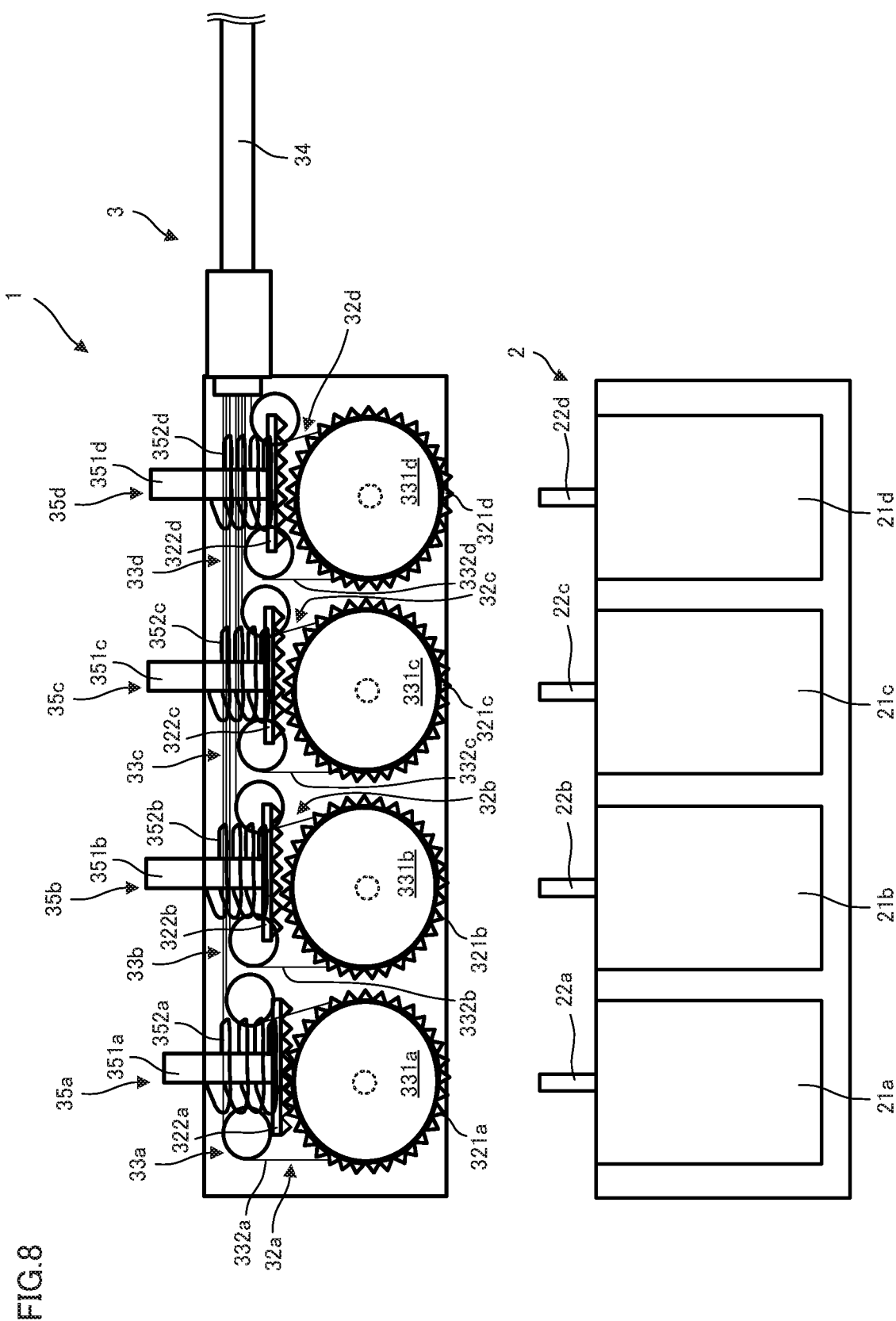
FIG. 8 shows the lock unit and driving force transmission unit in the manipulator of the first example according to the second embodiment.

FIGS. 7A, 7B and 7C show a first example of the manipulator 1 according to the second embodiment, and FIG. 8 shows a lock unit 32 and a driving force transmission unit 33 of the manipulator 1 according to the first example of the second embodiment. Note here that the manipulator 1 described just below has much the same arrangement as explained with reference to FIGS. 5A, 5B, 5C and 5D: that same arrangement will not be referred to anymore.

As shown in FIGS. 7A, 7B and 7C, the manipulator 1 of the first example according to the second embodiment includes an open/close grasping part 311 at the distal end 31. The distal end 31 includes a first joint 31a that rotates as the drive unit 2 is driven to open or close the grasping part 311 and a plurality of second 31b to fourth joint 31d that rotate as the drive unit 2 is driven. The grasping part 311 opens or closes as the drive unit 2 is driven to rotate the first joint 31a, enabling the grasping part 311 to take grasp of a tissue piece T or the like. The distal end 31 changes in shape as the second 31b, third 31c and fourth joint 31d rotate. It is here to be noted that the end effector attached to the distal end 31 is not limited to the grasping part 311; it may be any desired treatment equipment such as an electric scalpel or an injector.

As shown in FIGS. 7A, 7B and 7C, the manipulator 1 of the first example according to the second embodiment is configured such that the locking of the joints at the distal end and the attachment/detachment of the treatment tool 3 to/out of the drive unit 2 are feasible in one operation. With detachment from the drive unit 2, the weight of the treatment tool 3 reduces, making it easy to pull the treatment tool 3 from the body.

As shown in FIG. 8, the drive unit 2 in the manipulator 1 of the first example according to the second embodiment includes first drive member 21a to fourth drive member 21d in association with the first joint 31a to fourth joint 31d shown in FIGS. 7A, 7B and 7C. Then, the manipulator 1 of the first example includes, in association with the first drive member 21a to fourth drive member 21d, first output shaft 22a to fourth output shaft 22d, first lock portion 32a to fourth lock portion 32d, first driving force transmission portion 33a to fourth driving force transmission portion 33d, and first locking portion 35a to fourth locking portion 35d. It is here to be understood that the portions in association with the first drive member 21a to fourth drive member 21d are structurally the same; only the portions in association with the first drive member 21a are explained just below.

The driving force generated by the first drive member 21a is produced out of the first output shaft 22a and transmitted to the first driving force transmission portion 33a because the axis of the first output shaft 22a is coupled to the center hole in a first gearwheel pulley 331a. The first driving force transmission portion 33a includes the first gearwheel pulley 331a coupled to the first output shaft 22a, and a first wire 332a that is attached at both ends to the distal end 31 and wound around the first gearwheel pulley 331a. The first gearwheel pulley 331a is rotated by the driving force produced out of the first output shaft 22a to let out and take up the first wire 332a so that the first joint 31a at the distal end 31 shown in FIGS. 7A, 7B and 7C are rotated to open and close the grasping part 311.

The first lock portion 32a includes a first gearwheel 321a formed at the first gearwheel pulley 331a and first mating teeth 322a that mate with the first gearwheel 321a. The first lock-operating portion 35a includes a first operation switch 351a for actuating the first mating teeth 322a and first gearwheel 321a in a disengaging fashion, and a first coil spring 352a for biasing the first mating teeth 322a. The first lock-operating portion 35*a* is preferably built up of the first operating switch 351*a* and first coil spring 352*a* that define together a toggle switch.

A control unit (not shown) controls the first drive member 21*a* to put the joint 31*a* at the distal end 31 shown in FIGS. 7A, 7B and 7C into operation. As the first operating switch 351*a* of the first lock-operating portion 35*a* is depressed down, it causes the first mating teeth 322*a* of the first lock portion 32*a* to mate with the first gearwheel 321*a* with the result that the first joint 31*a* shown in FIGS. 7A, 7B and 7C are locked because the first gearwheel pulley 331*a* is incapable of rotation. That is, the first joint 31*a* is locked while the grasping part 311 remains closed. Note here that this embodiment may use a single lock-operating unit 35 to lock all the lock portions 32.

It is understood that the structure of the manipulator 1 according to the second embodiment is not limited to the described one and may otherwise be designed; mating with the drive unit may otherwise be achieved. For instance, the lock unit 32 is described as having a structure including the gear 321 and mating teeth 322, but that structure may otherwise be locked in place. The lock-operating unit 35 is described as a toggle switch, but it is not limited to such a mechanical toggle switch; reliance may also be on a slide switch or other desired mechanism capable of locking and unlocking. The switch may be biased on one side. Further, control may be performed via a structure in which an electrical signal is sent by a switch to control the locking and unlocking of the lock unit 32 by means of an electrically operated member (not shown) through a control unit (not shown). When an electric scalpel is used at the distal end 31, an insulating member may be inserted between a high-frequency output device (not shown) and the treatment tool to physically shut off output.

Figure 9:
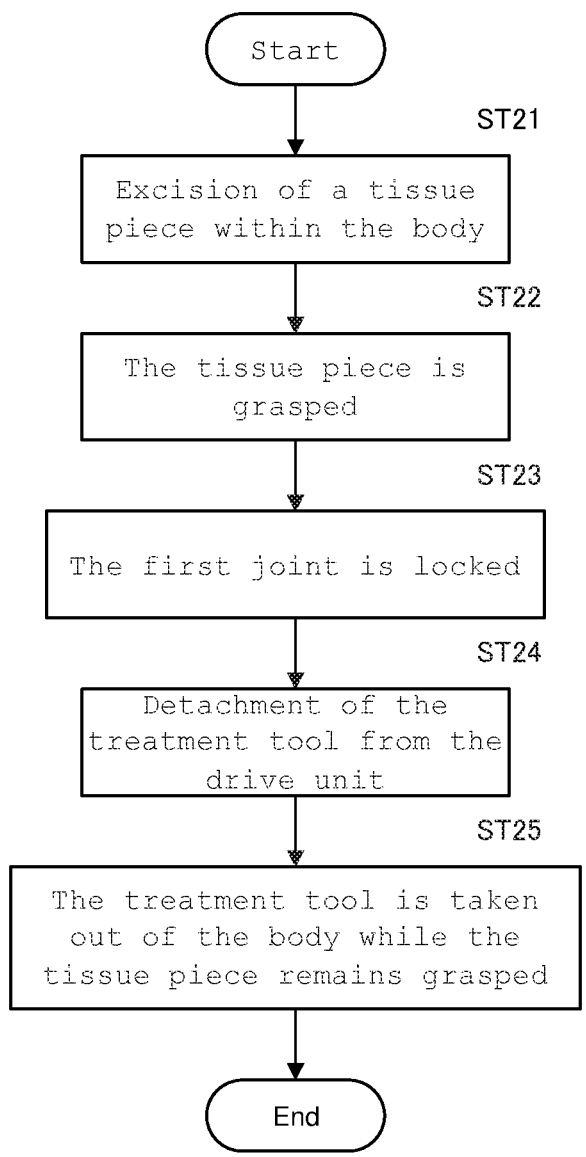
FIG. 9 is an actuation flowchart for the manipulator of the first example according to the second embodiment.

FIG. 9 is an actuation flowchart for the manipulator 1 of the first example according to the second embodiment. In the first example of the second embodiment, the process of taking the tissue T shown in FIGS. 7A, 7B and 7C out of an internal organ is explained from the step of excising that tissue.

In Step 21, at least a portion of the tissue piece T is first excised by the grasping part 311 from an internal organ O as shown in FIG. 7A (ST21).

In Step 22, the tissue piece T excised out of the internal organ O is then grasped by the grasping part 311 as shown in FIG. 7B (ST22).

In Step 23, the first joint 31*a* is then locked (ST23). The first joint 31*a* shown in FIG. 7B is locked by depressing down the first operating switch 351*a* of the first operating portion 35*a* to mate the first mating teeth 322*a* of the first lock portion 32*a* with the first gearwheel 321*a* thereby keeping the first gearwheel pulley 331*a* against rotation, as shown in FIG. 8.

In Step 24, the treatment tool 3 is then detached from the drive unit 2 (ST24) by means of a detachment switch (not shown) or the like, as shown in FIG. 7B. With the treatment tool 3 detached from the drive unit 2, only the first joint 31*a* locked by the first lock portion 32*a* remains fixed as shown in FIG. 8, but the rest or the second 31*b* to the fourth joints 31*d* are placed in a free-state capable of rotation.

In Step 25, the treatment tool 3 is then pulled out of the body with the tissue piece T remained grasped (ST25). Because the first joint 31*a* remains fixed at this time, the tissue piece T is pulled while remains fixed, and because the rest or the second joint 31*b* to the fourth joint 31*d* are placed in the free-state capable of rotation, they are pulled by the elongated member 34 and extended in a straight line. Thus, it is possible to pull the treatment tool 3 easily out of the body while the tissue piece T remains grasped. It is here to be noted that as a tube 36 that covers over the elongated member 34 is provided, it enables the second joint 31*b* to the fourth joint 31*d* to be housed in that tube 36, ensuring that the treatment tool 3 can more smoothly be taken out of the body.

Figure 10A:
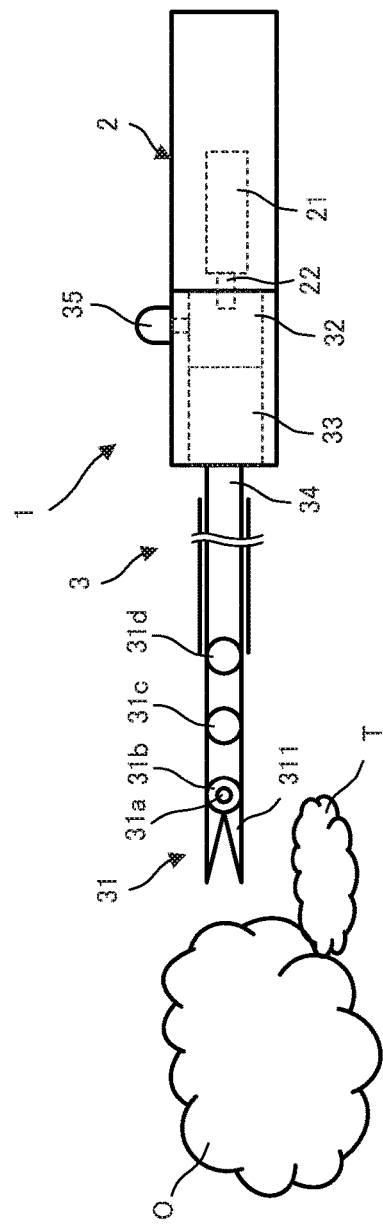
FIGS. 10A, 10B and 10C show the second example of the manipulator according to the second embodiment.
Figure 10B:
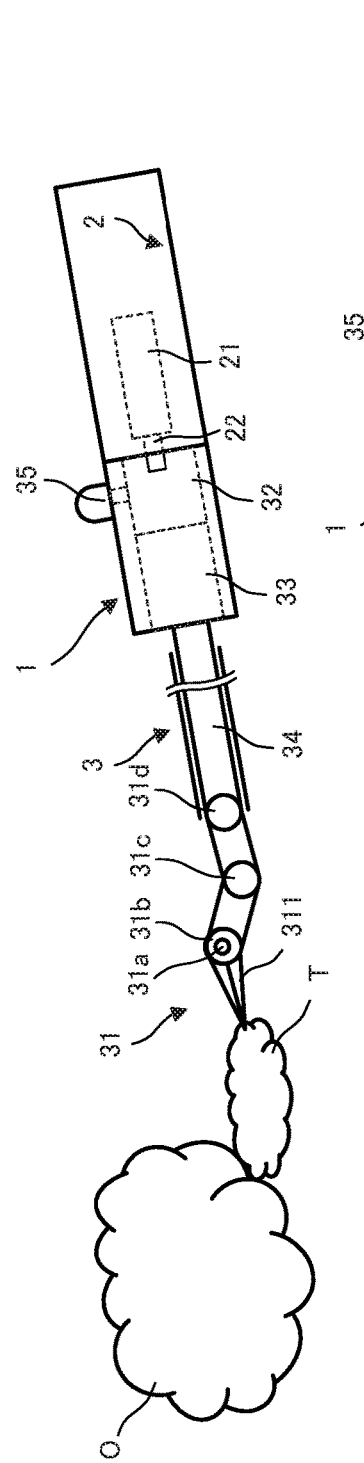
Figure 10C:
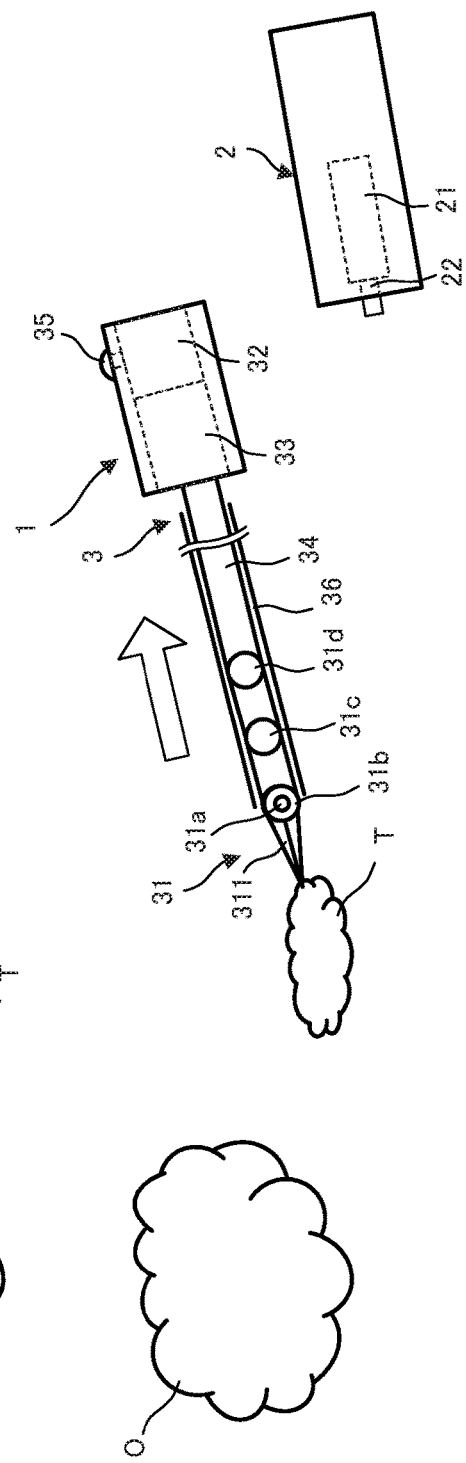

FIGS. 10A, 10B and 10C show the second example of the manipulator 1 according to the second embodiment.

In the manipulator 1 of the second example according to the second embodiment, the treatment tool 3 is detached from the drive unit 2 by means of the lock-operating unit 35. In other words, the lock-operating unit 35 of the second example works locking the joint assembly 31 and disengaging the treatment tool 3 out of the drive unit 2, as shown in FIG. 10C.

As described above, the lock-operating unit 35 has a dual function of locking the joint assembly 31 in place and disengaging the treatment tool 3 out of the drive unit 2 or performing two steps in one operation. It is thus possible to pull the treatment tool 3 more rapidly out of the body while the tissue piece T remains grasped there.

Figure 11A:
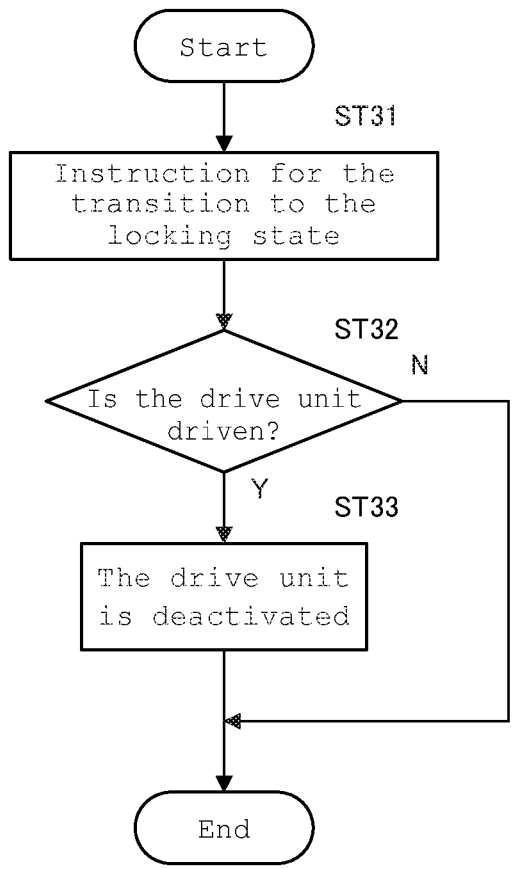
FIGS. 11A and 11B are flowcharts for the third example of the manipulator according to the second embodiment.
Figure 11B:
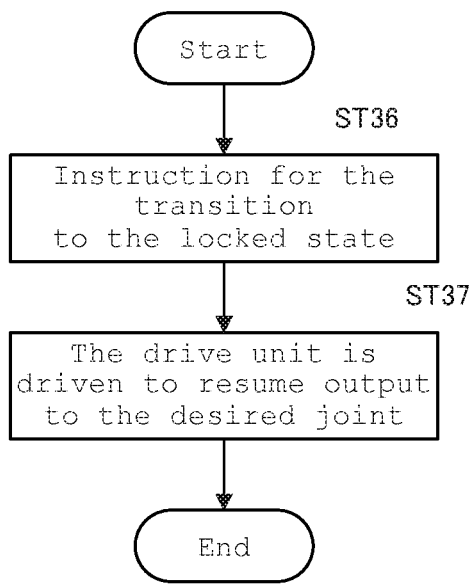

FIGS. 11A and 11B are a flowchart for the third example of the manipulator 1 according to the second embodiment: FIG. 11A is a flowchart for a transition to a locked state and FIG. 11B is a flowchart for unlocking.

The third example of the second embodiment is an example of operation of the manipulator 1 wherein the lock-operating unit 35 puts the lock unit 32 into operation during the driving of the drive unit 2. Control here is executed by a control unit (not shown).

The transition to the locked state shown in FIG. 11A will now be explained.

In Step 31, an instruction for the transition to the locked state is first entered (ST31), and the process then goes to Step 32 in which whether or not the drive unit 2 is put into actuation is determined (ST32). In Step 32, if the drive unit 2 is not actuated, the process waits for the next instruction. In Step 32, if the drive unit 2 is put into actuation, the process goes to Step 33 in which the drive unit 2 is deactivated to put the manipulator 1 into a locked state (ST33).

A transition to the clearing of deactivation shown in FIG. 11B will now be explained.

In Step 36, an instruction for the transition to the locked state is first entered (ST36), and the process goes to Step 37 in which the drive unit 2 is driven to resume output to the desired joint (ST37).

After the drive unit 2 is deactivated in Step 33, the treatment tool 3 may be detached from the drive unit 2 while the joint is locked. The first joint 31*a* shown typically in FIG. 7B may be locked by depressing down the first switch 351*a* of the first lock-operating portion 35*a* to mate the first mating teeth 322*a* of the first lock-operating portion 32*a* with the first gearwheel 321*a* thereby keeping the gearwheel pulley 331*a* against rotation. As the treatment tool 3 is detached from the drive unit 2, it causes only the first joint 31*a* locked by the first lock portion 32*a* while the rest or the second joint 31*b* to the fourth joint 31*d* are placed in a free state capable of rotation.

Thus, when the lock-operating unit 35 is operated in such a way as to be locked during the actuation of the drive unit 2, the drive unit 2 comes to a stop so that the joint assembly can rapidly be deactivated, thereby grasping back or reducing adverse influences of movement of the distal end on the surroundings.

Figure 13:
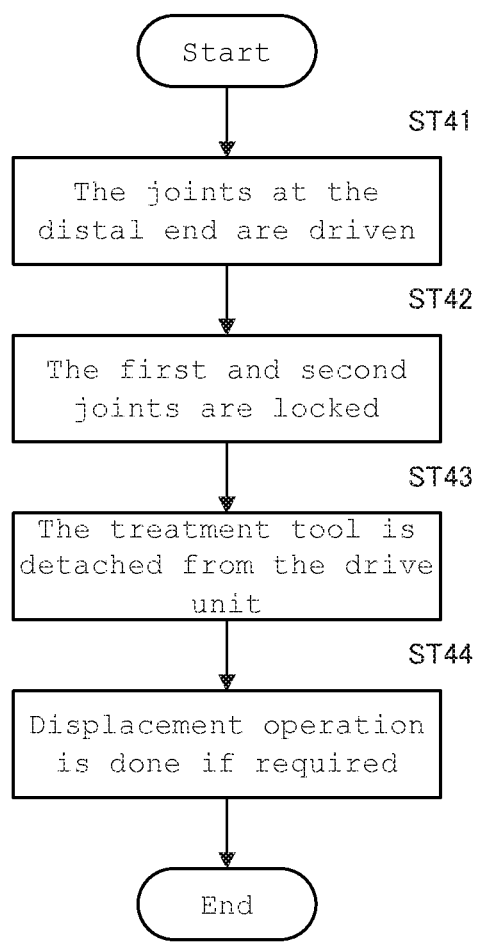
FIG. 13 is a flowchart for the fourth example of the manipulator according to the second embodiment.

FIGS. 12A, 12B and 12C show the fourth example of the manipulator 1 according to the second embodiment, and FIG. 13 is a flowchart for the fourth example of the manipulator 1 according to the second embodiment.

In the fourth example of the second embodiment, an internal organ is displaced. The manipulator 1 is structurally similar to that of FIGS. 7A, 7B and 7C.

In Step 41, the joint assembly at the distal end 31 is first driven in a given configuration as shown in FIGS. 12A and 1B (ST41). Preferably, the grasping part 311 should be directed oppositely to the internal organ O so that there is no damage to the internal organ O to be displaced.

The process then goes to Step 42 to lock the first 31a and second joint 31b (ST42). As shown in FIG. 8, the first joint 31a shown in FIG. 12B is locked by depressing down the first operating switch 351a of the first lock-operating portion 35a to mate the first mating teeth 322a of the first lock portion 32a with the first gearwheel 321a thereby keeping the first gearwheel pulley 331a against rotation.

In Step 43, the treatment tool 3 is then detached from the drive unit 2 (ST43). As shown in FIG. 12C, the treatment tool 3 is detached from the drive unit 2 by means of the lock-operating unit 35 or a detachment switch or the like (not shown). As the treatment tool 3 is detached from the drive unit 2, it causes the first joint 31a locked by the first lock portion 32a and the second joint 31b locked by the second lock portion 32b and the rest or the third 31c and fourth joint 31d to be placed in a free state capable of rotation.

In Step 44, displacement operation is then carried out if necessary (ST44) to get control done. In this example, the internal organ O is seized by a portion of the second joint 31b at the distal end 31 that is opposite to the grasping part 311 as shown in FIG. 12(b). Because the internal organ O is seized by the portion of the joint opposite to the grasping part 311, adverse influences on the internal organ to be displaced can be held back.

Figure 14:
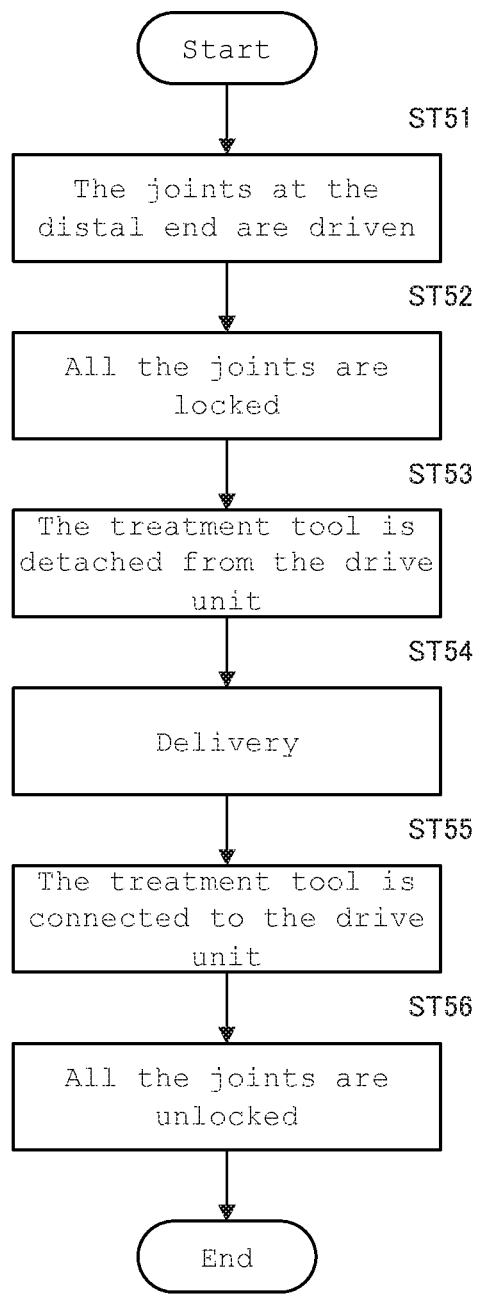
FIG. 14 shows the fifth example of the manipulator according to the second embodiment.

FIG. 14 shows the fifth example of the manipulator 1 according to the second embodiment.

The fifth example of the second embodiment is illustrative of how to deliver the manipulator 1 that is structurally similar to that of FIGS. 7A, 7B and 7C.

In Step 51, the joint assembly at the distal end 31 is first driven in a desired configuration (ST51). The distal end 31 should preferably be driven in a configuration for delivery.

In Step 52, all the joints 31a to 31d are locked (ST52). As shown in FIG. 8, the joints 31a to 31d are locked by depressing down the operating switches 351a to 351d of the lock-operating portions 35a to 35d to mate the mating teeth 322a to 322d of the lock portions 32a to 32d with the gearwheels 321a to 321d thereby keeping the gearwheel pulleys 331a to 331d against rotation.

In Step 53, the treatment tool 3 is then detached from the drive unit 2 (ST53). The treatment tool 3 is detached from the drive unit 2 by means of the lock-operating unit 35 or a detachment switch or the like (not shown). Even with the treatment tool 3 detached from the drive unit 2, the joints 31a to 31d locked by the lock portions 32a to 32d remain fixed.

In Step 54, the manipulator 1 is then delivered (ST54).

After delivery, the treatment tool 3 is connected to the drive unit 2 (ST55). Even with the treatment tool 3 connected to the drive unit 2, the joints 31a to 31d locked by the lock portions 32a to 32d remain fixed. It is thus possible to achieve unerring connection of the treatment tool 3 to the drive unit 2.

In Step 56, all the joints 31a to 31d are then unlocked (ST56). If the operator or an assistant again depresses down the operating switches 351a to 351d—built up of toggle switches or the like—of the lock-operating portions 35a to 35d to space the mating teeth 322a to 322d of the lock portions 32a to 32d away from the gearwheels 321a to 321d thereby keeping the gearwheel pulleys 331a to 331d against rotation, it is then possible to unlock all the joints 31a to 31d. Note here that the control unit (not shown) may be used to connect the treatment tool 3 to the drive unit 2 and, at the same time, unlock the joints.

As described above, all the joints 31a to 31d of the treatment tool 3 are fixed during delivery. It is thus possible to achieve stable delivery because there is no movement of the joints 31a to 31d even when there are loads resulting from vibrations or the like during delivery. It is also possible to get the treatment tool 3 ready for immediate use after all the joints 31a to 31d are unlocked after delivery.

Figure 15A:
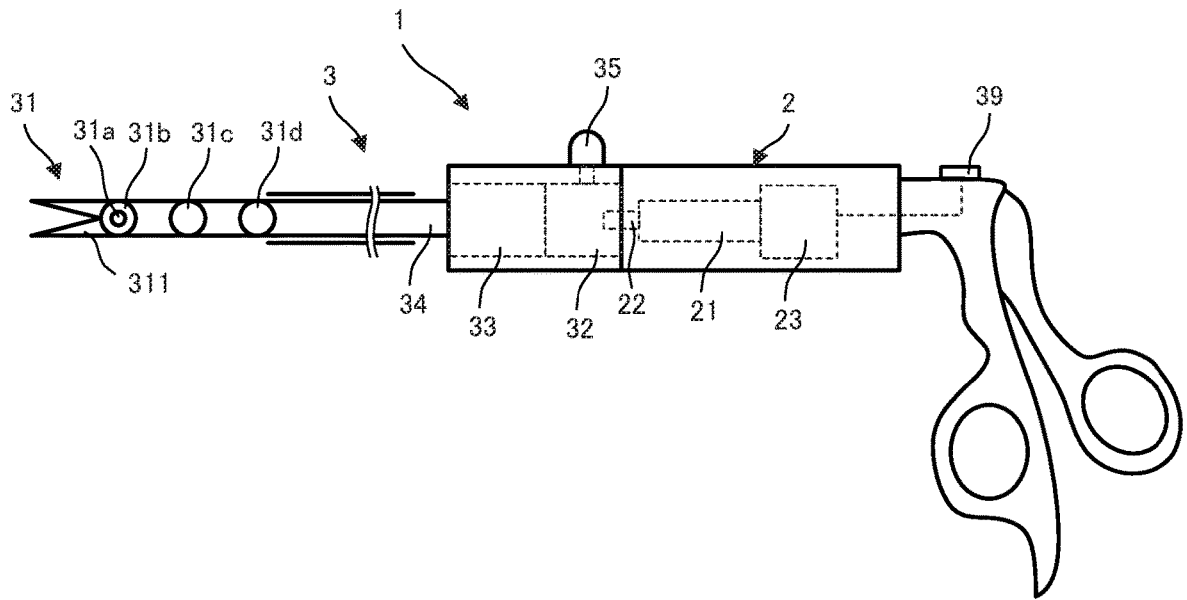
FIGS. 15A and 15B show the manipulator according to a further embodiment.
Figure 15B:
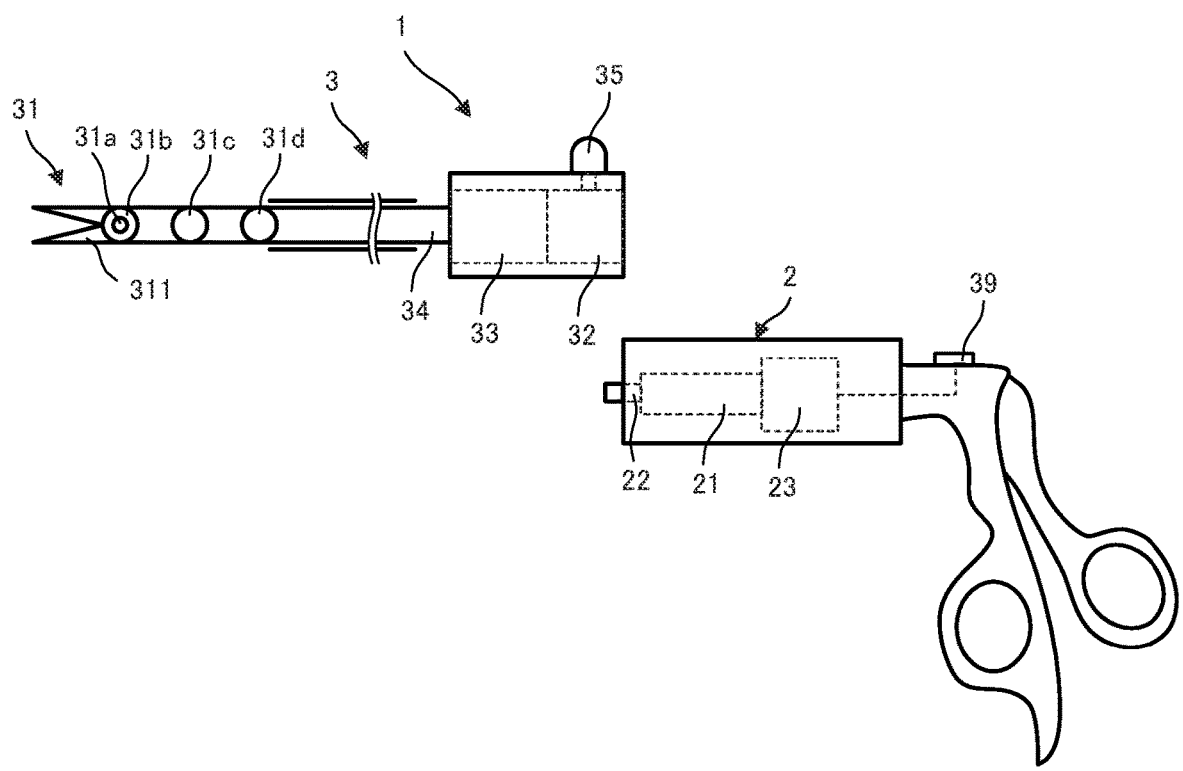

FIGS. 15A and 15B show the manipulator 1 according to a further embodiment: FIG. 15A is illustrative of the manipulator 1 in normal operation, and FIG. 15B is illustrative of the manipulator 1 upon pulling.

The manipulator 1 shown in FIGS. 15A and 15B includes a drive actuator 39 for operating a drive unit 2, and a lock-operating unit 35 for operating a lock unit 32, and the drive unit 2 and drive actuator 39 are provided in such a way as to be attached to or detached from the lock unit 32, etc. Note here that the drive unit 2 may be separate from the drive actuator 39.

In normal operation of the manipulator 1, the drive unit 2 is operated by the drive actuator 39 for operation of the distal end 31 of the treatment tool 3.

Upon pulling the manipulator 1 from the body cavity, the lock-operating unit 35 has a dual function in one operation: locking of the joints at the distal end 31 of the treatment tool 3 and attachment or detachment of the treatment tool 3 to or from the drive unit 2. Detachment from the drive unit 2 contributes to a weight reduction, ensuring easy pulling the treatment tool 3 from the body.

Figure 16:
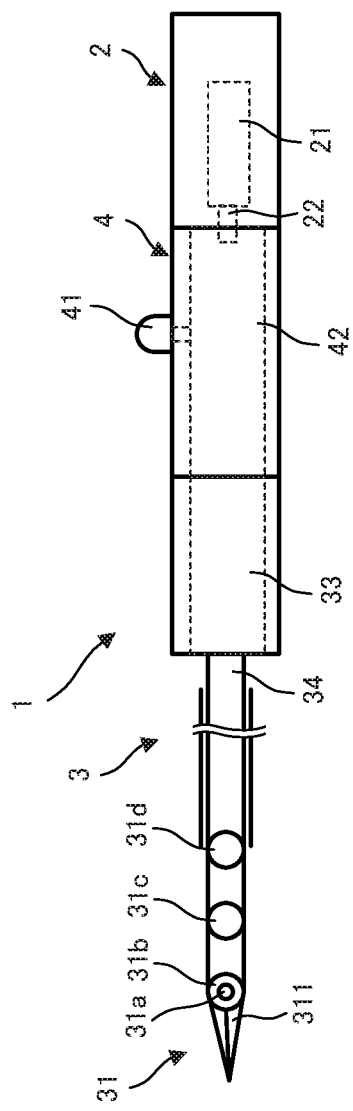
FIG. 16 shows the manipulator according to a further embodiment.

FIG. 16 shows the manipulator 1 according to a further embodiment.

The manipulator 1 shown in FIG. 16 includes an intermediate member 4 located between the drive unit 2 and the treatment tool 3. The intermediate member 4 is structurally attachable to or detachable from the drive unit 2 and the treatment tool 3, respectively. While the lock-operating unit 35 and lock unit 32 are provided on the treatment tool 3 in the example of FIGS. 7A, 7B and 7C, it is understood that in the embodiment of FIG. 16, the lock-operating unit 41 and lock unit 42 are provided on the intermediate member 4.

Such intermediate member 4 may be used in combination with existing treatment tool 3 and drive unit 2, contributing more to be flexible about design.

Relations of the manual joint operation function to the joint lock function of the treatment tool 3 connectable to the drive unit 2 are now explained. Reference is first made to the ability of the treatment tool 3 to be discretely operated.

The joint operation by the treatment tool 3 described here may have such functions as indicated by O in the following Table 1.

TABLE 1

|  | No manual joint function | Manual joint function |
|---|---|---|
| No joint lock function | X | ○ |
| Joint lock function | ○ | ○ |

Figure 17:
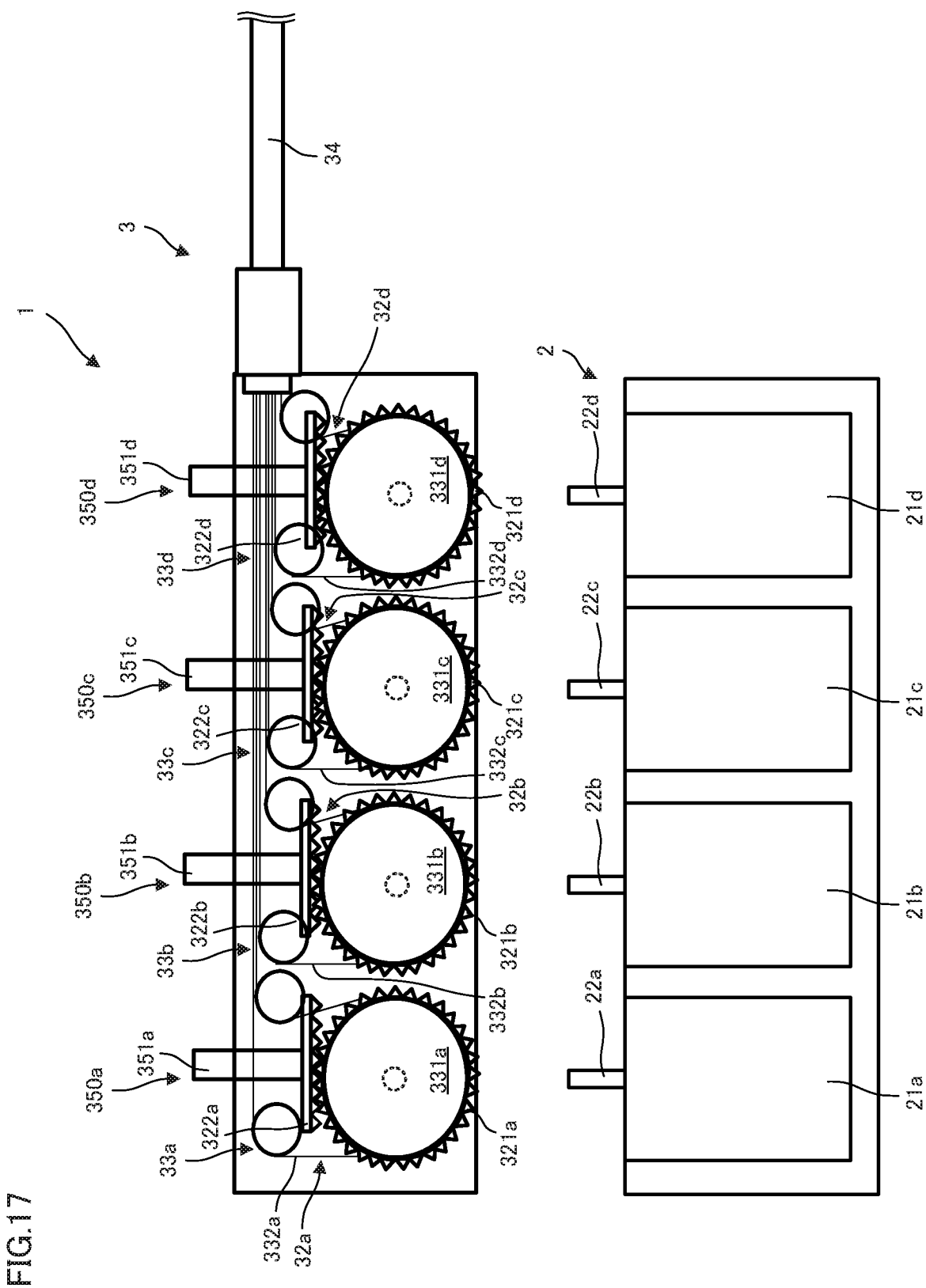
FIG. 17 shows the first example of the joint operation function of the treatment tool 3 according to a specific embodiment.

FIG. 17 is illustrative of the first example of the joint operation function of the treatment tool 3 described here.

In the first example of the joint function of the treatment tool 3, there is no joint lock function, but there is the manual joint operation function available. The treatment tool 3 of the first example is typically configured in such a way as to be driven by manual rotation of the operating unit 350. For instance, the operating unit 350 is provided for operation of the joints. As shown in FIG. 17, the operating unit 350 may be configured like a lever. Note here that the treatment tool 3 of the first example is connectable to the drive unit 2.

Figure 18:
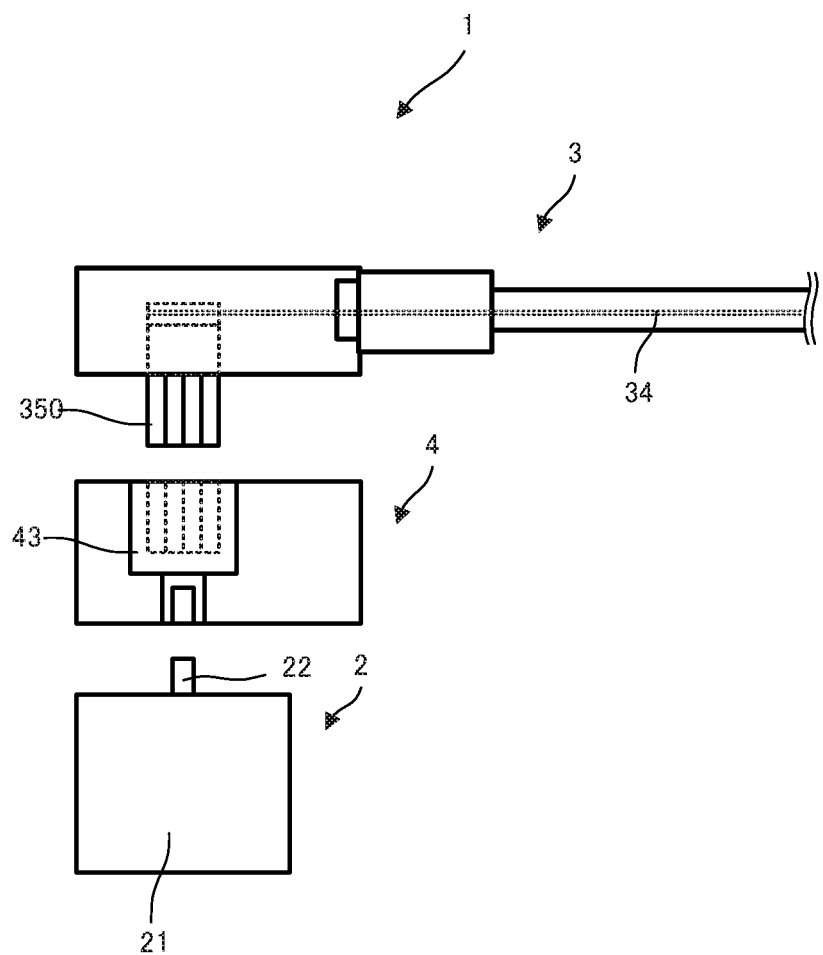
FIG. 18 shows a modification to the first example of the joint operation function of the treatment tool 3 according to a specific embodiment.

FIG. 18 shows a modification to the first example of the joint operation function of the treatment tool 3 described here.

The treatment tool 3 shown in FIG. 18 includes the operating unit 350 having a function of manually operating the joints, and is defined by a member having projections and depressions such as a gear and mating with one side of the junction 43 of the intermediate member 4. The other side of the junction 43 of the intermediate member 4 is joined to the output shaft 22 of the drive member 21. In other words, the operating unit 350 is mated with one side of the junction 43 of the intermediate member 4 and the driving shaft 22 is joined to the other side of the junction 43 so that the treatment tool 3 will be driven by the drive unit 2. It is thus possible to apply treatments by a master slave from a target position in which the joints of the treatment tool 3 are put into manual operation.

The second example of the joint operation function of the treatment tool 3 has a joint lock function, but has no joint operation function. In the treatment tool 3 of the second example, the lock-operating unit 35 is built up of a toggle type button that is depressed down thereby locking the joints, as shown typically in FIG. 8. In other words, the lock-operating unit 35 is provided to lock the joints. Note here that the lock-operating unit 35 may be defined by a lever or pin, and that the treatment tool 3 of the second example is connectable to the drive unit 2.

The third example of the joint operation function of the treatment tool 3 has both the joint lock function and the manual joint operation function. For instance, the treatment tool 3 of the third example includes the operating unit 350 for manual joint operation according to the first example, and the lock-operating unit 35 for locking the joints according to the second example, respectively. A single operating unit may be provided for both manual joint operation and joint lock operation. Note here that the treatment tool 3 of the third example is connectable to the drive unit 2.

How to operate the treatment tool 3 discretely is then explained.

The drive unit 2 and treatment tool 3 of the manipulator 1 include a master-slave mode of performing a master-slave operation and a standby mode in which there is no operation performed.

Figure 19:
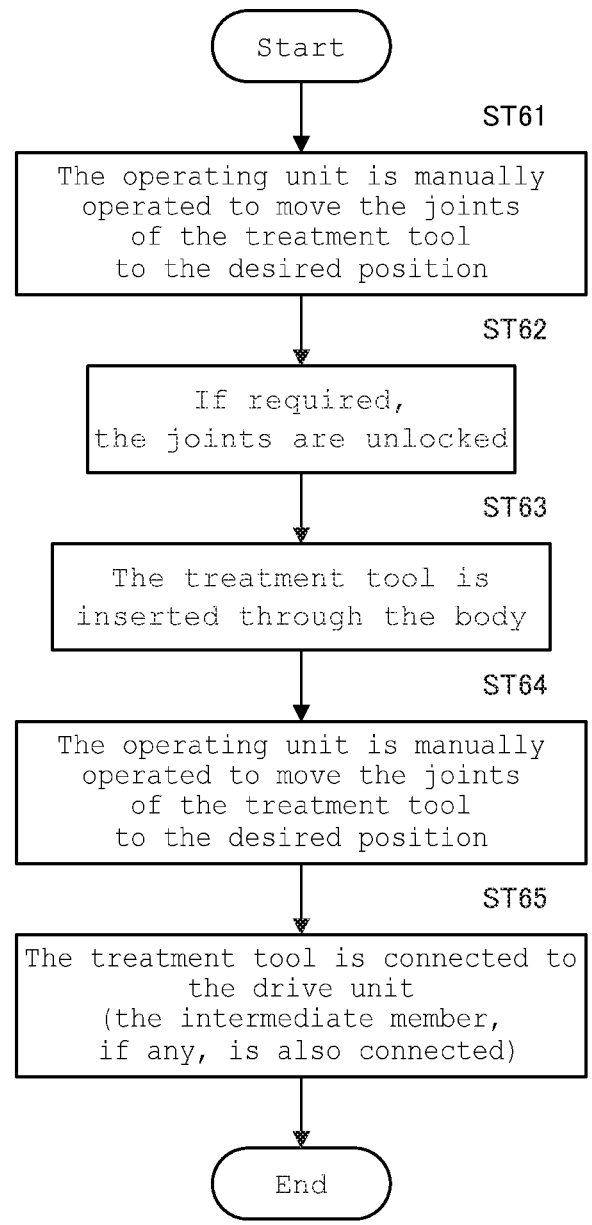
FIG. 19 is a flowchart for processing in the standby mode prior to the master-slave operation.

FIG. 19 is a flowchart indicative of processing in the standby mode prior to the master-slave operation.

In Step 61, the operating unit 350 is first manually operated to advance the joints of the treatment tool 3 to the desired position (ST61). It is here preferable that the joints should be placed in such a posture as to get ready for insertion through the body.

In Step 62, the joints are then unlocked if required (ST62).

In Step 63, the treatment tool 3 is then inserted through the body (ST63).

In Step 64, the operating unit 350 is then manually operated to move the joints of the treatment tool 3 to the desired position (ST64). It is here preferable that the joints should be moved to the target position for medical treatment to which the master-slave mode treatment is immediately applied.

In Step 65, the treatment tool 3 is then connected to the drive unit 2 (ST65). Note here that when the intermediate member 4 is used, it is also connected to the drive unit 2. As that connection is detected, there is a transition from the standby mode to the master-slave mode.

In the master-slave operation mode, the drive member 21 is driven or deactivated in association with the manual joint operation. In this case, it is preferable that there is an operation sensor (not shown) provided for the purpose of detecting a manual joint operation state.

For instance, there may be a cover or other similar mechanism provided for keeping the manual joint operation portion against operation at the time of connection of the treatment tool 3 to the drive unit 2, thereby grasping back unintended operation caused by manual operation during the operation of the treatment tool 3. Note here that when the manual joint operation is detected, the drive member 21 may be deactivated to issue a warning.

Alternatively, there may be a lever or other similar mechanism provided for enabling the manual joint operation portion to be operated to detach an attachment/detachment portion. After the joints are driven to any desired position by means of electrically forced operation, the manual joint operation may be carried out so that waste operation during treatments can be eliminated.

If clearing of the joint lock function is detected during the master-slave mode operation, there is then a transition to the standby mode, and if disconnection of the treatment tool 3 from the drive unit 2 is detected during the master-slave mode operation, there is then a transition to the standby mode.

Figure 20:
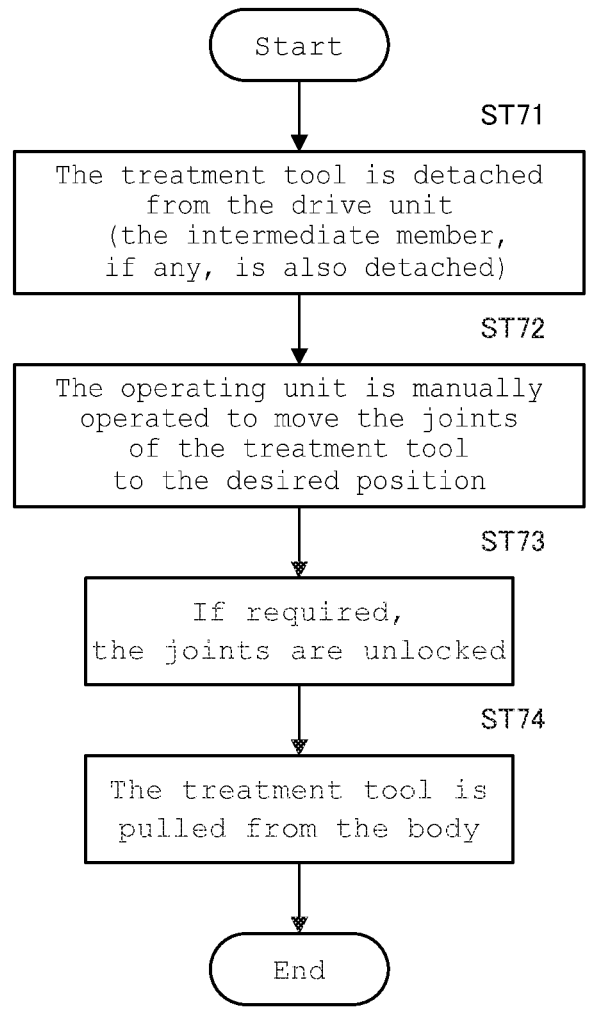
FIG. 20 is a flowchart for processing in the standby mode after the completion of the master-slave operation.

FIG. 20 is a flowchart indicative of the standby mode operation after the master-slave mode operation gets done.

In Step 71, the treatment tool 3 is first disconnected from the drive unit 3 (ST71). If disconnection of the treatment tool 3 is detected, there is then a transition from the master-slave mode to the standby mode. The unit for operation of the attachment/detachment of the drive unit 2 to and from the treatment tool 3 may be the same as the lock-operating unit for operation of the joint lock function. Note here that the intermediate member 4, if any, is also set free.

In Step 72, the operating unit 350 is first put into manual operation to move the joints of the treatment tool 3 to the desired portion (ST72). It is here preferable that they should be placed in a posture for getting ready for pulling.

Then, the joints are locked if required in Step 73 (ST73).

The treatment tool 3 is then pulled from the body in Step 74 (ST74). At this time, the treatment tool 3 is pulled from the body while at least one joint remains locked with a tissue peeled by forceps grasped in place. It is thus possible to take the tissue out of the body.

One possible embodiment wherein the manual joint operation function and joint lock function may be put by the intermediate member 4 into operation is now explained.

Understandably, the joint operation function of the intermediate member 4 described here would also be the same as that set out in Table 1.

Figure 21:
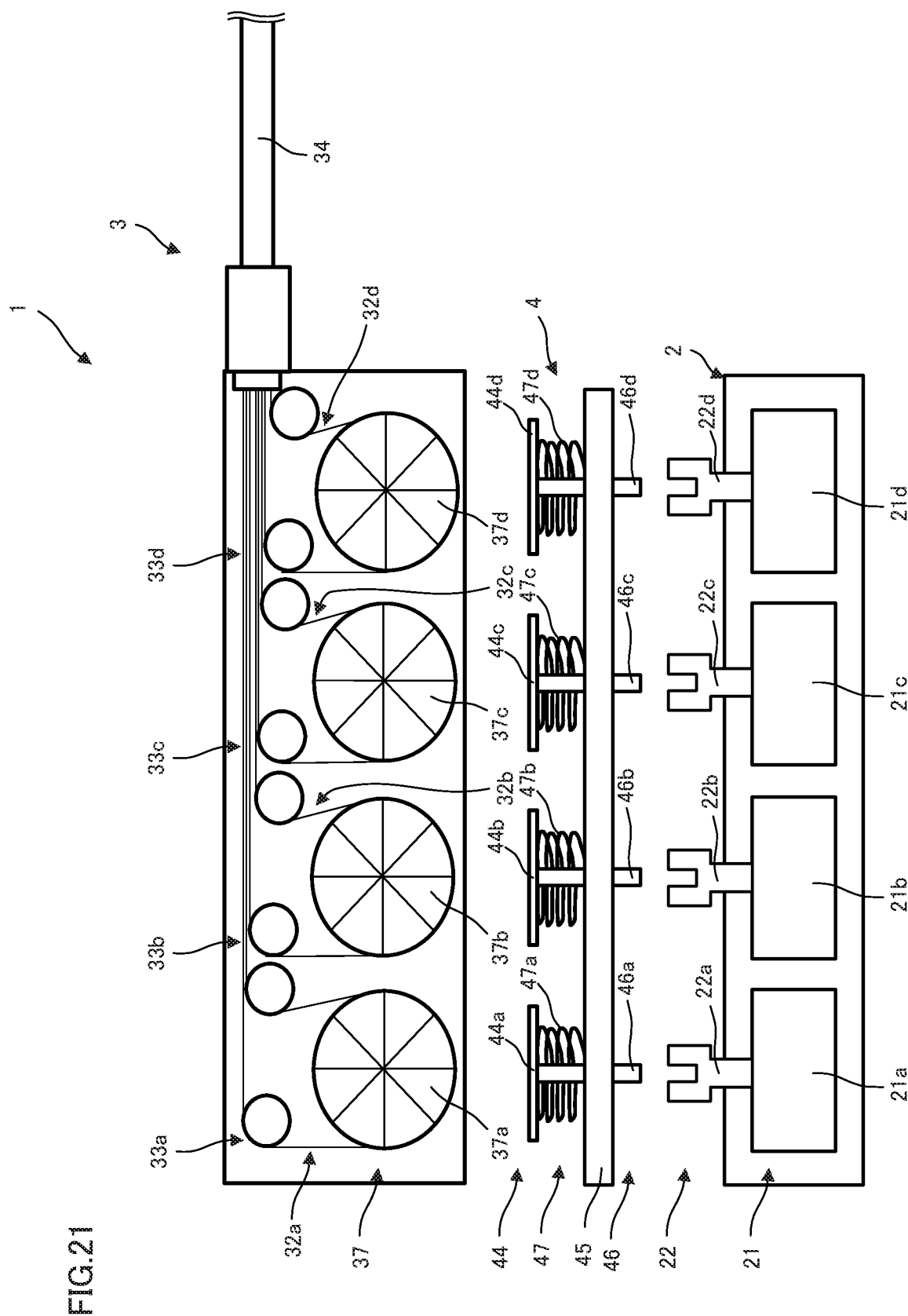
FIG. 21 shows the first example of the joint operation function of an intermediate member according a specific embodiment.

FIG. 21 shows the first example of the joint operation function of the intermediate member 4 described here.

The first example of the joint operation function of the intermediate member 4 has none of the joint lock function but has the manual joint operation function. In the first example, for instance, the treatment tool 3 and intermediate member 4 are coupled to each other by mating a mating portion 37 of the treatment tool 3 having projections and depressions with a mating portion 44 of the intermediate member 4 having projections and depressions. The mating portion 44 is provided at one end of a transmission unit 46 passing through the main unit 45, and the other end of the transmission unit 46 is connectable to the output shaft 22 of the drive unit 2. The mating portion 44 is also biased by a spring 47 in a direction away from the main unit 45.

The intermediate member 4 having such structure is used to rotate the transmission unit 46. This in turn rotates the mating portion 37 of the treatment tool 3 mating therewith. That is, the transmission unit 46 of the intermediate member 4 has also a function of putting the joints of the treatment tool 3 into operation. Note here that the transmission unit 46 of the first example has a dual function of putting the joints of the treatment tool 3 into operation and transmitting the output of the drive unit 2; however, another separate member may be used for it.

Figure 22:
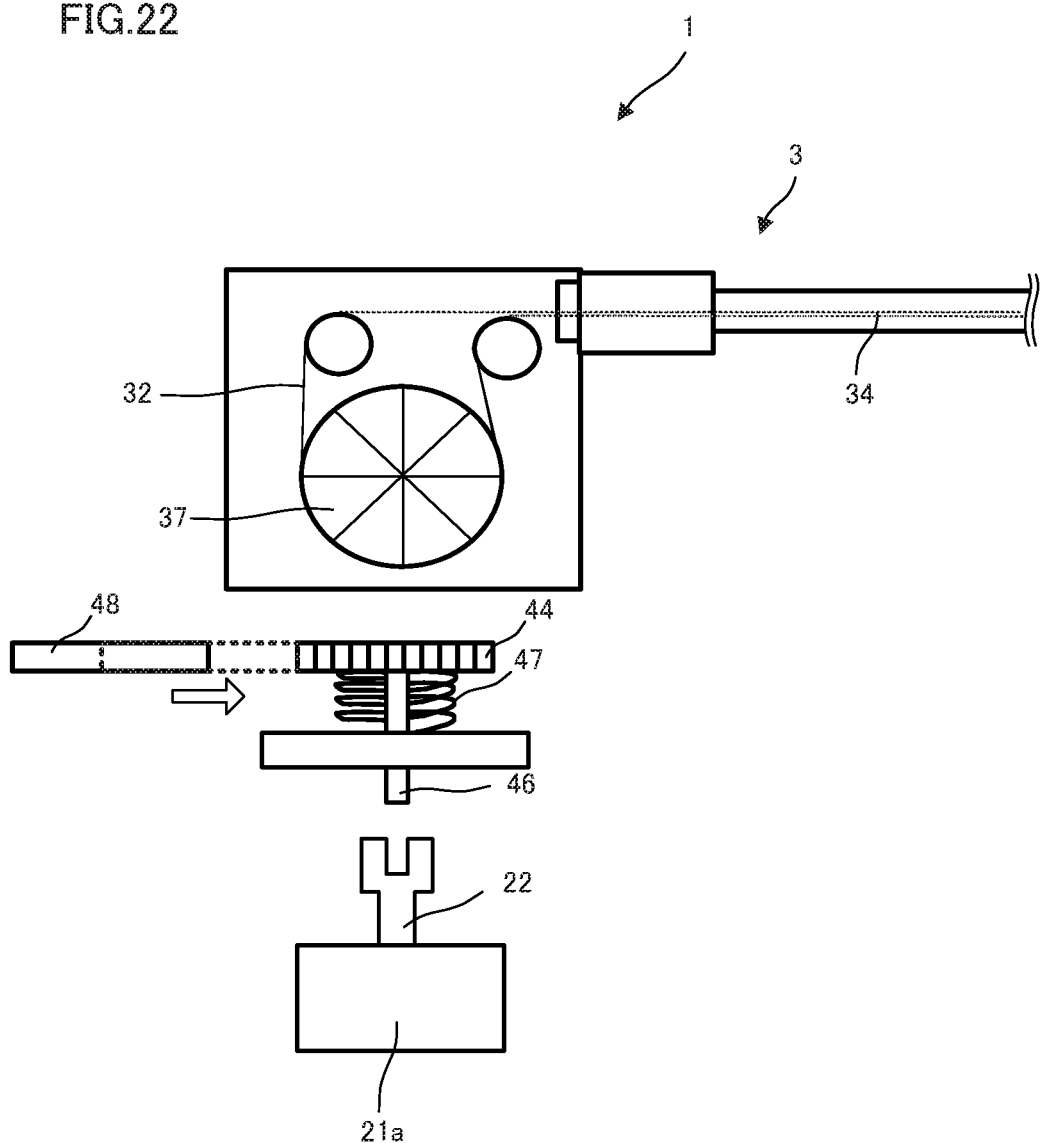
FIG. 22 shows the second example of the joint operation function of the intermediate member according to a specific embodiment.

FIG. 22 shows the second example of the joint operation function of the intermediate member 4 described here.

The second example of the joint operation function of the intermediate member 4 has a function of locking the joints, but does not have any manual joint operation function. As shown typically in FIG. 22, the intermediate member 4 of the second example includes projections and depressions on the side of the mating portion 44. As a toggle type button 48 is depressed down, it mates with the projections and depressions on the side of the mating portion 44 to immobilize and lock the joints. That is, the button 48 is provided for locking the joints. Note here that instead of the button 48 there may be a lever or pin used, and that the transmission unit 46 of the second example has not any function of putting the joints of the treatment tool 3 into operation.

The third example of the joint function of the treatment tool 3 has the function of locking the joints and the manual joint operation function. With the treatment tool 3 of the third example, for instance, the transmission unit 46 having a function of operating the joints of the treatment tool 3 of the first example and the button 48 having a function of locking the joints of the second example may be used.

In the manipulator 1 described here, it is possible to mount a plurality of intermediate members 4 corresponding to the first example to third example for each joint. For instance, the intermediate member 4 having only a manual joint operation function as in the first example may be used for the first joint, the intermediate member 4 having only a function of locking the second joint as in the second example may be used for the second joint, and the intermediate member 4 having both the manual joint operation function and the joint lock function as in the third example may be used for the third joint.

In addition, the manual joint operation function and joint lock function may be allocated to both the treatment tool 3 and intermediate member 4, respectively. For instance, the joint lock function may be allocated to the treatment tool 3 and the manual joint operation function to the intermediate member 4 and the vice versa.

How to run the manipulator 1 capable of being put by the intermediate member 4 into operation is now explained.

Figure 23:
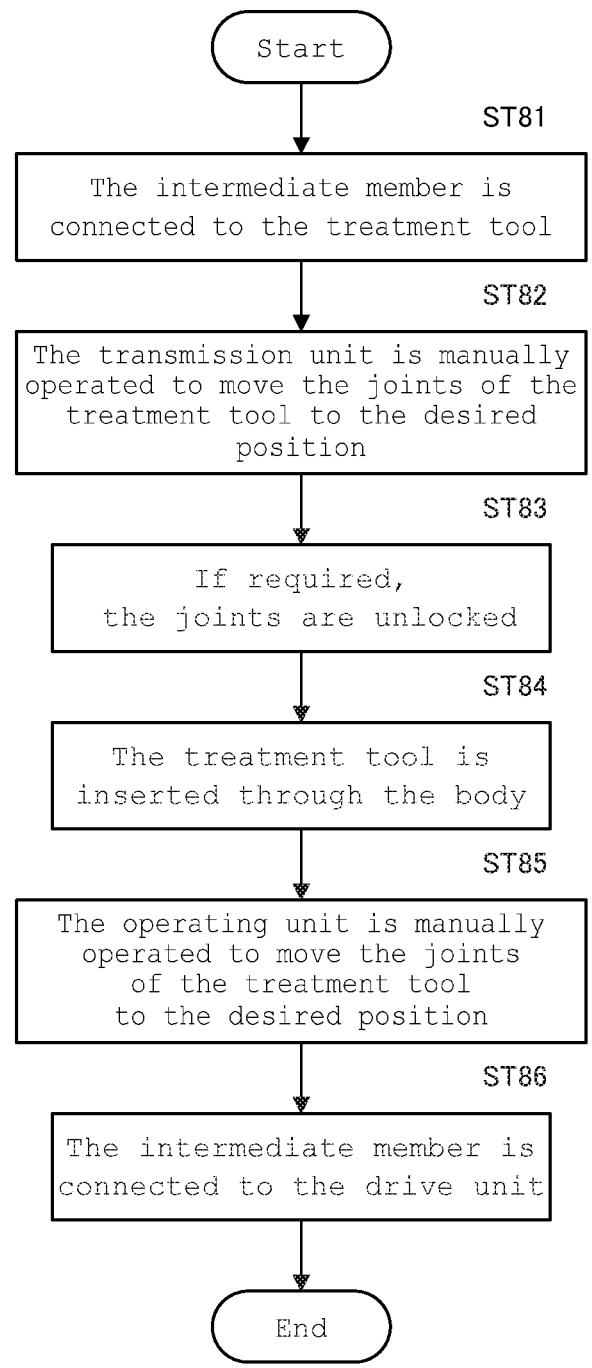
FIG. 23 is a flowchart for processing the standby mode prior to the master-slave operation.

FIG. 23 is a flowchart indicative of processing in the standby mode prior to the master-slave operation.

In Step 81, the intermediate member 4 is first connected to the treatment tool 3 (ST81).

Then, the process goes to Step 82 in which the transmission unit 46 is manually operated to move the joints of the treatment tool 3 to the desired position (ST82). It is here preferable that they should be placed in a posture for getting ready for insertion into the body.

The process then goes to Step 83 in which the joints are unlocked if required (ST83).

The process then goes to Step 84 in which the treatment tool 3 is inserted through the body (ST84).

The process then goes to Step 85 in which the transmission unit 46 is manually operated to move the joints of the treatment tool 3 to the desired position (ST85). It is here preferable that the master-slave treatments are immediately enabled in conformity with the target position in which they are performed.

The process then goes to Step 86 in which the drive unit 2 is connected to the intermediate member 4 (ST86). Upon detection of that connection, there is a transition from the standby mode to the master-slave mode.

Alternatively, when the joints being locked is detected upon connection of the drive unit 2 to the intermediate member 4 in Step 76, the joints may be unlocked. It is preferable that the mating portions of the drive unit 2, intermediate member 4 and treatment tool 3 are capable of rapidly mating with one upon another whatever relations they are in.

The manipulator system 100 using the manipulator 1 described herein will now be explained.

Figure 24:
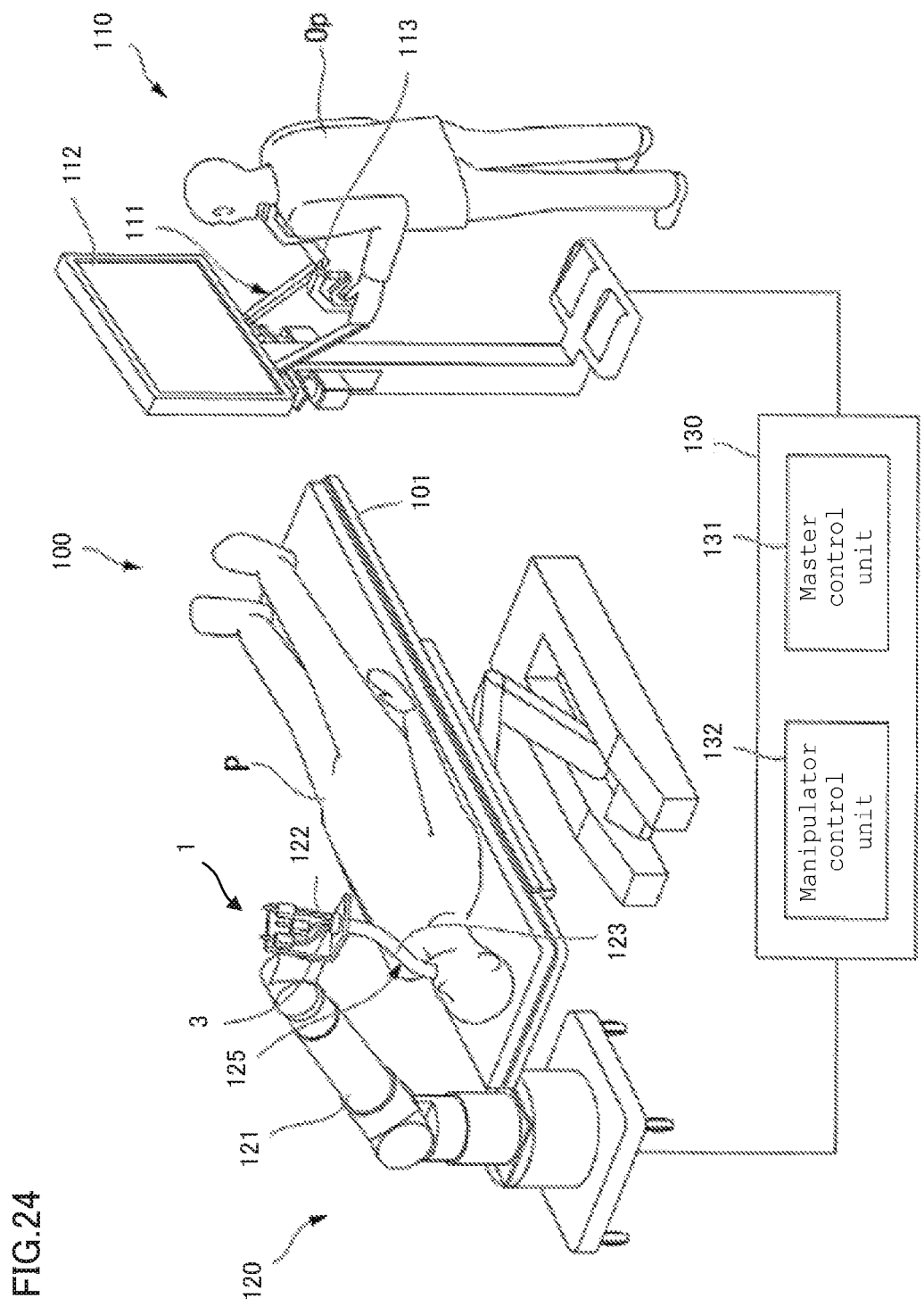
FIG. 24 shows the manipulator system using the manipulator according to a specific embodiment.

FIG. 24 shows the manipulator system 100 incorporating the manipulator 1 described herein.

Preferably, the manipulator system 100 described here runs in the master-slave mode. The manipulator system 100 includes a master input unit 110 including a master arm 111 for issuing an operation command, and a slave manipulator 120 including a slave arm 121, and the slave arm 121 is remotely controlled in such a way as to keep track of the master arm 111 operated by a surgeon (operator) Op. The operation command entered via the master arm 111 is sent out to the master controller 131 of a system control unit 130, and optionally subjected to transformation processing if required, after which it is entered in a manipulator control unit 132. Thereafter, an actuation signal is transmitted from the manipulator control unit 132 to the slave manipulator 120 to put the slave arm 121 into actuation.

As shown in FIG. 24, the slave manipulator 120 is mounted on an operating table 101 on which a patient P lies down. The slave arm 121 includes a plurality of multi-degrees of freedom joints, and is capable of multi-axis operations. The multi-degrees of freedom joints are discretely driven by a power unit (not shown). The power unit used here, for instance, may be a motor (servo motor) having a servo mechanism including an incremental encoder, decelerator or the like.

Attached to the distal end of the slave arm 121 are a manipulator 1 and an endoscope 122 that are inserted through the body of the patient P for surgical procedures. The treatment tool 3 and endoscope 122 are inserted through an overtube 123 to form an insert assembly 125. The distal end of the overtube 123 is inserted through the body of the patient P. A plurality of treatment tools 3 are selectively used for each surgical procedure, and have distal treatment portions varying in terms of structure and configuration. These treatment tools 3 are attached to the distal end of the slave arm 121 for each replacement. The endoscope 122 acquires images of a surgical field including a site where surgical procedures are performed by the treatment tool 3 within the body of the patient P.

The master input unit 110 includes a plurality of master arms 111 operated by the surgeon Op, and a display unit 112 for displaying images acquired by way of the endoscope 122. Each the master arm 111 has a known construction capable of multi-axis operations, and includes a grip portion 113 on the distal side near the surgeon Op, which portion acts as an operating portion gripped by the surgeon to issue an operation command.

Figure 25:
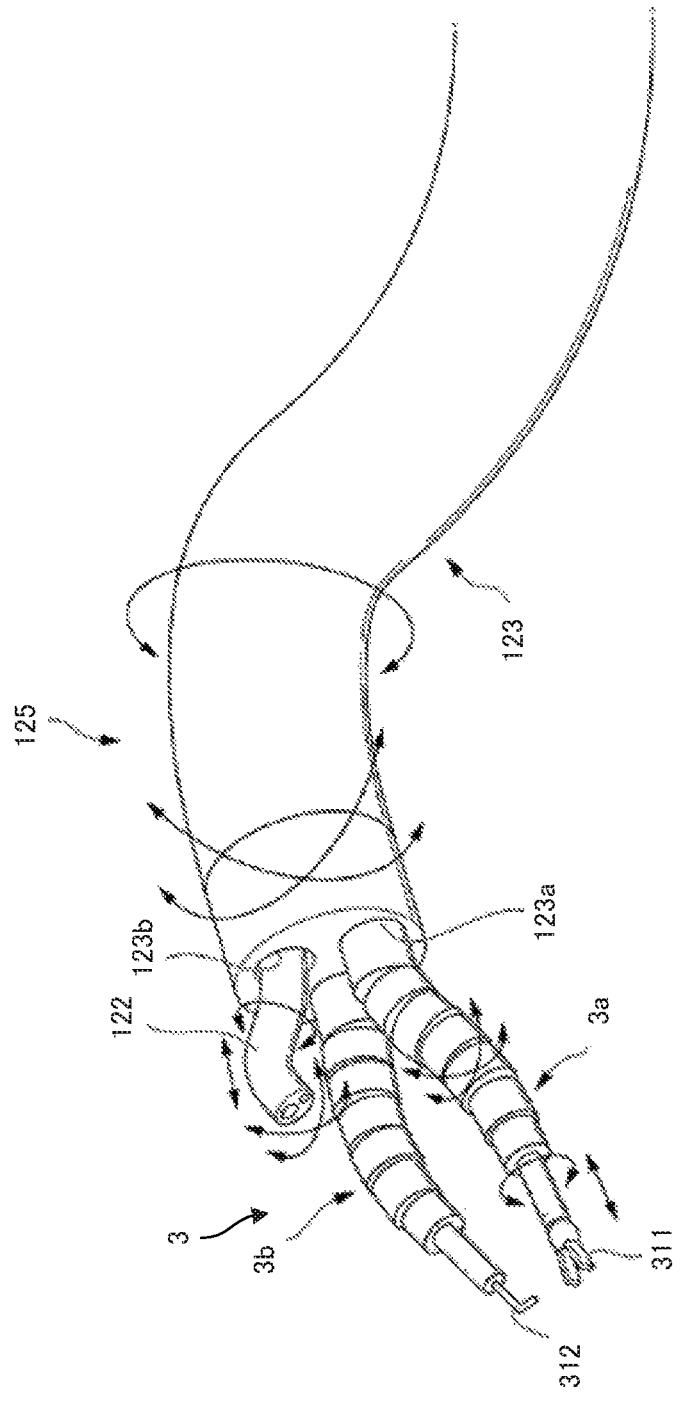
FIG. 25 is illustrative in construction of the insert assembly according to a specific embodiment.

FIG. 25 shows an exemplary construction of the insert assembly 125 described here.

The insert assembly 125 described here includes a flexible, elongated overtube 123, a treatment tool 3 inserted into an opening 123a in the overtube 123 for insertion of the treatment tool 3, and an endoscope 122 inserted into an opening 123b in the overtube 123 for insertion of the endoscope 122. Note here that the treatment tool 3 has a structure applicable to the manipulator system 1 described here.

According to a specific embodiment the treatment tool 3 described here includes a first treatment tool 3a and a second treatment tool 3b and, as an end effector, the first treatment tool 3a has a grasping part 311 while the second treatment tool 3b has an electrical scalpel 312. Being capable of projecting from the overtube 123, the distal end side of the treatment tool 3 is constructed of a bending assembly having a plurality of joint rings arranged in the axial direction. The most distal joint ring is fixedly provided with both ends of an operating wire for driving the bending assembly so that the bending assembly can be bent by driving the operating wire, and can be rotated in the axial direction as well.

The distal end of the endoscope 122 is also capable of projecting from the overtube 123, and it can be bent or rotated in the axial direction by driving a flexible, tubular member by way of an operating wire. It is preferable that the overtube 123 per se is also capable of being bent and rotated in the axial direction.

FIGS. 26A, 26B and 26C show the actuation of the insert assembly 125 described here.

As shown in FIGS. 26A, 26B and 26C, the manipulator 1 has a structure that is basically identical with that shown in FIGS. 7A, 7B and 7C. The insert assembly 125 shown in FIGS. 26A, 26B and 26C include the elongated member 34 covered over by the overtube 123. In this example, it is thus possible to house the second joint 31b to fourth joint 31d within the overtube 123 so that the treatment tool 3 can more smoothly be pulled from the body.

FIGS. 27A and 27B show the actuation of the insert assembly 125 described here.

As shown in FIGS. 27A and 27B, the manipulator 1 has a structure that is basically identical with that shown in FIGS. 15A and 15B. The insert assembly 125 shown in FIGS. 27A and 27B include the elongated member 34 covered over by the overtube 123. In this example, it is thus possible to house the second joint 31b to fourth joint 31d within the overtube 123 so that the treatment tool 3 can more smoothly be pulled from the body.

The manipulator 1 according to the embodiments described so far includes a treatment tool 3 operated by an tool-operating unit 38, and the treatment tool 3 includes a distal end 31 having at least one joint operated by the tool-operating unit 38 and a lock unit 32 for locking at least one of joints at the distal end 31. It is thus possible to unerringly lock at least a portion of the distal end 31 in a given actuation state.

In the manipulator 1 according to one embodiment, the treatment tool 3 includes an assist drive unit 36 for assisting the tool-operating unit 38 in performing operation. It is thus possible to perform smooth operations.

The manipulator 1 according to the embodiments described so far includes a treatment tool 3 operated by a treatment tool-operating unit 38, and the treatment tool 3 includes a distal end 31 having at least one joint operated by the treatment tool-operating unit 38 and a lock unit 32 for locking at least one of joints at the distal end 31. After used in the body, and when a tissue piece T is taken out from the body in this example, the tissue piece T can be taken out while it remains grasped and locked by the distal end 31. It is thus possible to take out the tissue piece T easily from the body.

In the manipulator 1 described herein, the treatment tool 3 includes an assist drive unit for assisting the treatment tool-operating unit in adding a driving force to its operating force. It is thus possible to provide easy operation of the treatment tool 3 and vary the actuation state of the distal end 31 with the result that the operation for taking a tissue piece T (not shown) out from the body is easily achievable.

The manipulator 1 according to the embodiments described so far includes a drive unit 2 adapted to generate a driving force, and a treatment tool 3 that is driven by the drive unit 2 to be attachable to and detachable from the drive unit 2, and the treatment tool 3 includes a distal end 31 having at least one joint driven by the drive unit 2 and a lock unit 32 for locking at least one of joints 31a to 31d at the distal end so that even with the drive unit 2 detached from the treatment tool 3, the lock unit 32 keeps on with locking. It is thus possible to pull the treatment tool 3 while at least one joint at the distal end 31 remains locked in a given actuation state, with the drive unit 2 detached from the treatment tool 3, and there is a weight reduction due to detachment from the drive unit 2, which makes it easier to operate the treatment tool 3.

In the manipulator 1 described herein, the treatment tool 3 includes a driving force transmission unit 33 for transmission of a driving force generated by the drive unit 2 to the distal end 31, and an elongated member 34 for coupling the distal end 31 to the driving force transmission unit 33, and the lock unit 32 blocks off transmission of the driving force at the driving force transmission unit 33. This makes sure unerring locking of at least one joint at the distal end 31 while placing it in a given actuation state.

In the manipulator 1 described herein, the treatment tool 3 includes a lock-operating unit 35 adapted to move the lock unit 32 to block off transmission of the driving force. This makes sure easy locking of at least one joint at the distal end 31 while placing it in a given actuation state.

In the manipulator 1 described herein, the drive unit 2 is attachable to and detachable from the driving force transmission unit 33, and the lock-operating unit 35 is operated thereby disengaging the drive unit out of the driving force transmission unit 33, and the transmission of driving force is blocked off by the lock unit 32. This enables two steps to be performed in one operation, and the treatment tool 3 to be more rapidly pulled from the body while at least one joint at the distal end remains placed in a given actuation state.

In the manipulator 1 described herein, the drive unit 2 includes a drive actuator 39 for driving the driving member 21 so that it is possible to drive the distal end 31 of the treatment tool 3 unerringly.

In the manipulator 1 described herein, the treatment tool 3 includes a lock sensor for detecting that the distal end 31 is locked by the lock unit 32 and a control unit that deactivates the driving of the drive unit 2 at the time when the lock sensor detects that the distal end 31 is locked by the lock unit 32. It is thus possible to deactivate the actuation of joints rapidly in emergency thereby grasping back or reducing adverse influences of movement of the distal end on surroundings.

In the manipulator 1 described herein, the treatment tool 3 is configured such that when the treatment tool 3 is connected to the drive unit 2 in a state of detachment from the treatment tool 3 out of the drive unit 2 and locking of the distal end 31 by the lock unit 32, the locking of the distal end 31 by the lock unit 32 is cleared in response to an operation by the lock-operating unit 35 or a command from control unit. It is thus possible for a surgeon or assistant to unlock the distal end 31 or to perform automatic unlocking by the control unit so that the distal end 31 can rapidly be placed in an enabling state.

In the manipulator 1 described herein, the distal end 31 includes a grasping part 311 for grasping a tissue piece, and the grasping part 311 is capable of being opened and closed by a joint 31a. It is thus possible to pull the treatment tool 3 while the distal end 31 remains locked with a tissue piece T grasped by it thereby taking out the tissue piece T unerringly.

In addition, the manipulator system 100 described herein includes a master input unit 110 for issuing an operation command and a slave manipulator 120 including a manipulator 1, and the slave manipulator 120 is remotely controlled in such a way as to keep track of operation of the master input unit 110. It is thus possible to use the manipulator system 100 in places to which an operator does not gain access, thereby making effective use of limited space.

The manipulator system 100 described herein includes a flexible, elongated overtube 123, an endoscope 122 inserted into the overtube 123 and the manipulator 1 including a treatment tool 3 inserted into the overtube 123. It is thus possible to pull the treatment tool 3 while at least a portion of the distal end 31 remains locked in a given posture with the treatment tool 3 detached from the drive unit 2.

It is here to be appreciated that the invention is in no sense limited to such embodiments as described above. While the explanation of some embodiments embraces numerous specific details for illustration, it would be obvious to those skilled in the art that diverse variations or modifications made thereto are included within the scope of the invention. In other words, illustrative embodiments of the invention are described without excluding generality from the claimed inventions and imposing any limitation thereon.

REFERENCE SIGNS LIST

1: Manipulator
2: Drive unit
21: Driving member
22: Output shaft
3: Treatment tool
31: Distal end
311: grasping part
31a to 31d: Joints
32: Lock unit
33: Driving force transmission unit
34: Elongated member
35: Lock-operating unit
38: Treatment tool-operating unit
4: Intermediate member
41: Lock-operating unit
42: Lock unit
100: Manipulator system

The invention claimed is:

1. A manipulator, comprising:
a driver for generating a driving force, and
a treatment tool that is driven by the driver and attachable to and detachable from the driver, wherein the treatment tool includes:
a distal end having at least one joint driven by the driver,
a lock unit that is actuated to lock at least one of the joints at the distal end,
a lock-operating unit for operating the lock unit, and
a controller configured to operate such that the lock unit is operated by the lock-operating unit and such that when the driver is driven, the driver is deactivated, and even with the treatment tool detached from the driver, the lock unit keeps on with locking.

2. The manipulator according to claim 1,
wherein the treatment tool includes:
a driving force transmitter that transmits of a driving force generated by the driver to the distal end, and
an elongated member that couples the distal end to the driving force transmitter, wherein the lock unit blocks off transmission of a driving force at the driving force transmitter.

3. The manipulator according to claim 2,
wherein the driver is attachable to and detachable from the driving force transmitter, and the lock-operating unit is operated thereby disengaging the driver out of the driving force transmitter and blocking off the transmission of driving force by the lock unit.

4. The manipulator according to claim 1,
wherein the treatment tool is configured such that when the treatment tool is connected to the driver in a state of detachment of the treatment tool out of the driver and locking of the distal end by the lock unit, the locking of the distal end by the lock unit is cleared by operation of the lock-operating unit or a command from the controller.

5. The manipulator according to claim 1,
wherein the distal end includes a grasping part that grasps a tissue piece,
the grasping part is opened and closed by the joints.

6. A manipulator system comprising:
a master manipulator for issuing an operation command, and
a slave manipulator including a manipulator according to claim 1, wherein:
the slave manipulator is remotely controlled in such a way as to keep track of operation of the master manipulator.

7. A manipulator system, including:
a flexible, elongated overtube,
an endoscope inserted into the overtube, and
a manipulator according to claim 1, the manipulator comprising a treatment tool inserted into the overtube.

* * * * *